US008722332B2

(12) United States Patent
Prichard et al.

(10) Patent No.: US 8,722,332 B2
(45) Date of Patent: May 13, 2014

(54) **MACROCYCLIC LACTONE RESISTANCE MARKER FOR *DIROFILARIA IMMITIS***

(75) Inventors: Roger Prichard, Ste-Anne-de-Bellevue (CA); Catherine Bourguinat, Montreal (CA); Timothy Geary, Ste-Anne-de-Bellevue (CA); Rudolf Schenker, Basel (CH)

(73) Assignees: The Royal Institution for the Advancement of Learning/McGill University, Montreal, Quebec (CA); Novartis AG, Basel (CH)

( * ) Notice: Subject to any disclaimer, the term of this patent is extended or adjusted under 35 U.S.C. 154(b) by 0 days.

(21) Appl. No.: 13/638,799

(22) PCT Filed: Mar. 30, 2011

(86) PCT No.: PCT/CA2011/050169

§ 371 (c)(1), (2), (4) Date: Jan. 16, 2013

(87) PCT Pub. No.: WO2011/120165
PCT Pub. Date: Oct. 6, 2011

(65) Prior Publication Data

US 2013/0137669 A1 May 30, 2013

Related U.S. Application Data

(60) Provisional application No. 61/319,982, filed on Apr. 1, 2010.

(51) Int. Cl.
*A61K 31/495* (2006.01)

(52) U.S. Cl.
USPC ........................ 435/6.11; 424/405; 424/191.1

(58) Field of Classification Search
USPC ...................... 435/6.12, 6.11; 424/405, 191.1
See application file for complete search history.

(56) References Cited

U.S. PATENT DOCUMENTS

| | | | |
|---|---|---|---|
| 4,683,159 | A | 7/1987 | Bohrer et al. |
| 4,683,202 | A | 7/1987 | Mullis |
| 4,965,188 | A | 10/1990 | Mullis |

FOREIGN PATENT DOCUMENTS

| | | | |
|---|---|---|---|
| EP | 0979278 | B1 | 9/2007 |
| WO | WO98/49294 | A1 | 11/1998 |

OTHER PUBLICATIONS

Ardelli BF, Guerriero SB, Prichard RK. Characterization of a half-size ATP-binding cassette transporter gene which may be a useful marker for ivermectin selection in *Onchocerca volvulus*. Mol Biochem Parasitol. Jan. 2006;145(1):94-100. Epub Oct. 6, 2005.*
Bazzocchi C et al. Combined ivermectin and doxycycline treatment has microfilaricidal and adulticidal activity against *Dirofilaria immitis* in experimentally infected dogs. Int J Parasitol. Oct. 2008;38(12):1401-10. Epub Mar. 21, 2008.*
Bourguinat C, Ardelli BF, Pion SD, Kamgno J, Gardon J, Duke BO, Boussinesq M, Prichard RK. P-glycoprotein-like protein, a possible genetic marker for ivermectin resistance selection in *Onchocerca volvulus*. Mol Biochem Parasitol. Apr. 2008;158(2):101-11. Epub Dec. 14, 2007.*
McCall JW. The safety-net story about macrocyclic lactone heartworm preventives: a review, an update, and recommendations. Vet Parasitol. Oct. 24, 2005;133(2-3):197-206. Epub Apr. 26, 2005. Review.*

13638799 Blast Search (hits to Seq ID No. 1): Jul. 29, 2013 performed on http://blast.ncbi.nlm.nih.gov/Blast.*

Genbank Accession No. HM596853.2- *Dirofilaria immitis* P-glycoprotein gene, partial cds. (GI: 327204533, submitted by Bourginat C. et al. Jun. 23, 2010, retrieved on Jul. 29, 2013 from http://www.ncbi.nlm.nih.gov/nuccore/HM596853).*

McManus et al. (1984): Histopathologic features of canine heartworm microfilarial infection after treatment with ivermectin. Am J Vet Res 45:91-7.

Mealey (2008): Canine ABCB1 and macrocyclic lactones: heartworm prevention and pharmacogenetics. Vet Parasitol 158:215-22.

Molento et al. (2008): Anthelmintic resistant nematodes in Brazilian horses. Vet Rec 162:384-5.

Needleman et al. (1970): A general method applicable to the search for similarities in the amino acid sequence of two proteins. J Mol Biol 48:443-53.

Njue et al. (2004): Mutations in the extracellular domains of glutamate-gated chloride channel alpha3 and beta subunits from ivermectin-resistant *Cooperia oncophora* affect agonist sensitivity. J Neurochem 89:1137-47.

Orita et al. (1989): Detection of polymorphisms of human DNA by gel electrophoresis as single-strand conformation polymorphisms. Proc Nati Acad Sci U S A 86:2766-70.

(Continued)

*Primary Examiner* — Kenneth R. Horlick
*Assistant Examiner* — Olayinka Oyeyemi
(74) *Attorney, Agent, or Firm* — Ann R. Pokalsky, Esq.; Dilworth & Barrese, LLP

(57) ABSTRACT

The invention relates to a method for determining the responsiveness of a *Dirofilaria* spp. nematode to a macrocyclic lactone, by determining the genotype of the nematode at a position in a P-glycoprotein gene of the nematode corresponding to position 11, and optionally to position 618, in SEQ ID NO: 1, wherein the genotype GG at a position corresponding to position 11, or at positions corresponding to positions 11 and 618, in SEQ ID NO: 1 indicates that the nematode is likely resistant to the macrocyclic lactone. The invention also relates to methods for selecting a treatment to treat an animal infected with macrocyclic lactone resistant *Dirofilaria* spp nematode, and treating the animal; or for selecting a prophylactic to prevent an animal from becoming infected with a macrocyclic lactone resistant *Dirofilaria* spp nematode, and providing the prophylactic to the animal. The invention further relates to an isolated nucleic acid having at least 80% sequence identity to SEQ ID NO: 1.

18 Claims, 6 Drawing Sheets

(56) References Cited

OTHER PUBLICATIONS

Osei-Atweneboana et al. (2007): Prevalence and intensity of *Onchocerca volvulus* infection and efficacy of ivermectin in endemic communities in Ghana: a two-phase epidemiological study. Lancet 369:2021-9.
Pearson et al. (1988): Improved tools for biological sequence comparison. Proc Natl Acad Sci U S A 85:2444-8.
Prichard (2005): Is anthelmintic resistance a concern for heartworm control? What can we learn from the human filariasis control programs? Vet Parasitol 133:243-53.
Rubin et al. (2010): Diagnosis, prevention and management of heartworm infection in dogs: Guidelines, canine heartworm disease. American Heartworm Society. (revised Jan. 2010).
Saiki et al. (1986): Analysis of enzymatically amplified beta-globin and HLA-DQ alpha DNA with allele-specific oligonucleotide probes. Nature 324:163-6.
Sangster et al. (1999): *Haemonchus contortus*: sequence heterogeneity of internucleotide binding domains from P-glycoproteins. Exp Parasitol 91:250-7.
Smith et al. (1981): Comparison of biosequences. Adv Appl Math 2(4): 482-289.
Strote et al. (1996): The ultrastructure of the anterior end of male *Onchocerca volvulus*: papillae, amphids, nerve ring and first indication of an excretory system in the adult filarial worm. Parasitology 113 (Pt 1):71-85.
Tatusova et al. (1999): Blast 2 Sequences, a new tool for comparing protein and nucleotide sequences. FEMS Microbiol Lett 174:247-50.
Trawford et al. (2005): Suspected moxidectin resistance in cyathostomes in two donkey herds at the Donkey Sanctuary, UK. Abstracts of the 20th International Conference of the World Association for the Advancement of Veterinary Parasitology, Christchurch, New Zealand. p. 196.
Venco et al. (2004): Efficacy of long-term monthly administration of ivermectin on the progress of naturally acquired heartworm infections in dogs. Vet Parasitol 124:259-68.
Wolstenholme et al. (2004): Drug resistance in veterinary helminths. Trends Parasitol 20:469-76.
Xu et al. (1998): Ivermectin resistance in nematodes may be caused by alteration of P-glycoprotein homolog. Mol Biochem Parasitol 91:327-35.
GenBank accession No. HM596850, in Bourguinat et al. (2011): Genetic polymorphism in *Dirofilaria immitis*. Vet Parasitol 176:368-73.
Ali et al. (2002): Immunocompetence may be important in the effectiveness of Mectizan (ivermectin) in the treatment of human onchocerciasis. Acta Trop 84:49-53.
Altschul et al. (1990): Basic local alignment search tool. J Mol Biol 215:403-10.
Ardelli et al. (2004): Identification of variant ABC-transporter genes among *Onchocerca volvulus* collected from ivermectin-treated and untreated patients in Ghana, West Africa. Ann Trop Med Parasitol 98:371-84.
Ardelli et al. (2005): Genomic organization and effects of ivermectin selection on *Onchocerca volvulus* P-glycoprotein. Mol Biochem Parasitol 143:58-66.
Ardelli et al. (2006): Ivermectin imposes selection pressure on P-glycoprotein from *Onchocerca volvulus*: linkage disequilibrium and genotype diversity. Parasitology 132:375-86.
Ardelli et al. (2006): Characterization of a half-size ATP-binding cassette transporter gene which may be a useful marker for ivermectin selection in *Onchocerca volvulus*. Mol Biochem Parasitol 145:94-100.
Ardelli et al. (2007): Reduced genetic variation of an *Onchocerca volvulus* ABC transporter gene following treatment with ivermectin. Trans R Soc Trop Med Hyg 101:1223-32.
Atkins (2002): Canine Heartworm Disease: Current Treatment and Prevention Approaches.: "The 26th annual Waltham Diets/OSU Symposium. Small Animal Cardiology."
Awadzi et al. (2004): Thirty-month follow-up of sub-optimal responders to multiple treatments with ivermectin, in two onchocerciasis-endemic foci in Ghana. Ann Trop Med Parasitol 98:359-70.
Awadzi et al. (2004): An investigation of persistent microfilaridermias despite multiple treatments with ivermectin, in two onchocerciasis-endemic foci in Ghana. Ann Trop Med Parasitol 98:231-49.
Bennett et al. (1988): Pharmacology of ivermectin. Parasitol Today 4:226-8.
Blackhall et al. (1998): Selection at a P-glycoprotein gene in ivermectin- and moxidectin-selected strains of *Haemonchus contortus*. Mol Biochem Parasitol 95:193-201.
Blackhall et al. (1998): *Haemonchus contortus*: selection at a glutamate-gated chloride channel gene in ivermectin-and and moxidectin-selected strains. Exp Parasitol 90:42-8.
Blackhall et al. (2003): Selection at a gamma-aminobutyric acid receptor gene in *Haemonchus contortus* resistant to avermectins/milbemycins. Mol Biochem Parasitol 131:137-45.
Boersema et al. (2002): Apparent resistance of *Parascaris equorum* to macrocylic lactones. Vet Rec 150:279-81.
Bourguinat et al. (2007): Genetic selection of low fertile *Onchocerca volvulus* by ivermectin treatment. PLoS Negl Trop Dis 1:e72:12-22.
Bourguinat et al. (2008): P-glycoprotein-like protein, a possible genetic marker for ivermectin resistance selection in *Onchocerca volvulus*. Mol Biochem Parasitol 158:101-11.
Bourguinat et al. (2010): Geographical genetic polymorphism in *Dirofilaria immitis*. American Heartworm Society—State of the Heartworm Symposium 2010, Apr. 15-17, 2010 (abstract only).
Bourguinat et al. (2011): Genetic polymorphism in *Dirofilaria immitis*. Vet Parasitol 176:368-73.
Bourguinat et al. (2011): Macrocyclic lactone resistance in *Dirofilaria immitis*. Vet Parasitol 181:388-92.
Bourguinat et al.(2011): Correlation between loss of efficacy of macrocyclic lactone heartworm anthelmintics and P-glycoprotein genotype. Vet Parasitol 176:374-81.
Bourguinat et al. (2011): Macrocyclic lactone resistance in *Dirofilaria immitis*. Annual Meeting Proceedings—Sustainable Parasite and Vector Control. 56th Annual Meeting of the American Association of Veterinary Parasitologists, 55th Annual Meeting of the LIWC and 11th Annual Meeting of the ISEP, Jul. 16-19, 2011 (abstract only).
Bourguinat et al. (2012): Investigation of genetic changes in the genome of *Dirofilaria immitis* after the use of macrocyclic lactones as heartworm preventatives. Complementary Alliances: Veterinary, Human and Agrochemical Approaches to Parasiticides. 57th Annual Meeting of the American Association of Veterinary Parasitologists, Aug. 4-7, 2012 (abstract only).
Bowman et al. (1992): Effects of long-term administration of ivermectin and milbemycin oxime on circulating microfilariae and parasite antigenemia in dogs with patent heartworm infections. In: "Proceedings of the Heartworm Symposium '92." Austin, Texas, USA.: American Heartworm Society, Batavia, IL (USA), pp. 151-158.
Bowman et al. (2001): Effects of avermectins on microfilariae in dogs with existing and developing heartworm infections. In: Seward RL (Ed.) Recent Advances in Heartworm Disease: Symposium '02. American Heartworm Society, Batavia, IL; 173-178.
Bowman et al. (2006): The effects of preventative dosages of macrolide treatments on circulating microfilariae in dogs with patent heartworm-*Dirofilaria immitis* infections. US Companion Animal Health; 9-11.
Bowman et al. (2009): Heartworm biology, treatment, and control. Vet Clin North Am Small Anim Pract 39:1127-58, vii.
Bowman (2012): Heartworms, macrocyclic lactones, and the specter of resistance to prevention in the United States. Parasites & Vectors 5: 138-47.
Churcher et al. (2008): An analysis of genetic diversity and inbreeding in *Wuchereria bancrofti*: implications for the spread and detection of drug resistance. PLoS Negl Trop Dis 2:e211 (1-9).
Coles et al. (2006): The detection of anthelmintic resistance in nematodes of veterinary importance. Vet Parasitol 136:167-85.

(56) References Cited

OTHER PUBLICATIONS

Courtney et al. (1998): The effect of chronic administration of milbemycin oxime and ivermectin on microfilaremias in heartworrn-infected dogs. In: Seward RL (Ed.) Recent Advances in Heartworm Disease: Symposium '98. Amer. Heartworm Soc, Batavia, IL, pp. 193-199.
De Lourdes Mottier et al. (2008): Genetic analysis of a relationship between macrocyclic lactone and benzimidazole anthelmintic selection on *Haemonchus contortus*. Pharmacogenet Genomics 18:129-40.
Dent et al. (2000): The genetics of ivermectin resistance in *Caenorhabditis elegans*. Proc Natl Acad Sci U S A 97:2674-9.
Eng et al. (2005): A comparison of genetic polymorphism in populations of *Onchocerca volvulus* from untreated- and ivermectin-treated patients. Mol Biochem Parasitol 142:193-202.
Eng et al. (2006): Ivermectin selection on beta-tubulin: evidence in *Onchocerca volvulus* and *Haemonchus contortus*. Mol Biochem Parasitol 150:229-35.
Feng et al. (2002): Study of the nematode putative GABA type-A receptor subunits: evidence for modulation by ivermectin. J Neurochem 83:870-8.
Geary (2005): Ivermectin 20 years on: maturation of a wonder drug. Trends Parasitol 21:530-2.
Geary et al. (2010): Genetic changes in *Dirofilaria immitis* populations possibly associated with exposure to macrocyclic lactones. Parasite Evolution: Veterinary Parasites and Their Strategies to Survive Human Intervention. 55th Annual Meeting of the American Association of Veterinary Parasitologists, Jul. 31-Aug. 3, 2010 (abstract only).
Hampshire (2005): Evaluation of efficacy of heartworm preventive products at the FDA. Vet Parasitol 133:191-5.
Hearn et al. (2003): Identification of foals infected with *Parascaris equorum* apparently resistant to ivermectin. J Am Vet Med Assoc 223:482-5, 455.
Juliano et al. (1976): A surface glycoprotein modulating drug permeability in Chinese hamster ovary cell mutants. Biochim Biophys Acta 455:152-62.
Kaplan (2004): Drug resistance in nematodes of veterinary importance: a status report. Trends Parasitol 20:477-81.
Kaplan et al. (2004): Prevalence of anthelmintic resistant cyathostomes on horse farms. J Am Vet Med Assoc 225:903-10.
Le Jambre et al. (1999): A hybridisation technique to identify anthelmintic resistance genes in *Haemonchus*. Int J Parasitol 29:1979-85.
Lespine et al. (2008): ABC transporter modulation: a strategy to enhance the activity of macrocyclic lactone anthelmintics. Trends in Parasitol 24 (7): 293-98.
Lespine et al. (2009): Interaction of macrocyclic lactones with the multidrug transporters: the bases of the pharmacokinetics of lipid-like drugs. Curr Drug Metab 10:272-88.
Lespine et al. (2012): P-glycoproteins and other multidrug resistance transporters in the pharmacology of anthelmintics: prospects for reversing transport-dependent anthelmintic resistance. Int J Parasitol: Drugs and Drug Resistance 2: 58-75.
McCall et al. (1998): Heartworm adulticidal activity of prophylactic doses of ivermectin (6 pg/kg) plus pyrantel administered monthly to dogs. In: Seward RL (Ed.) Recent Advances in Heartworm Disease: Symposium '98. Amer. Heartworm Soc, Batavia, IL, pp. 209-215.
McCall (2005): The safety-net story about macrocyclic lactone heartworm preventives: a review, an update, and recommendations. Vet Parasitol 133:197-206.
McCall et al. (2008): Heartworm disease in animals and humans. Adv Parasitol 66:193-285.
GenBank accession No. HM596851, in Bourguinat et al. (2011): Genetic polymorphism in *Dirofilaria immitis*. Vet Parasitol 176:368-73.
GenBank accession No. HM596852, in Bourguinat et al. (2011): Genetic polymorphism in *Dirofilaria immitis*. Vet Parasitol 176:368-73.
GenBank accession No. HM596853, in Bourguinat et al. (2011): Genetic polymorphism in *Dirofilaria immitis*. Vet Parasitol 176:368-73.
GenBank accession No. HM596854, in Bourguinat et al. (2011): Genetic polymorphism in *Dirofilaria immitis*. Vet Parasitol 176:368-73.
Geary et al., "Evidence for Macrocyclic Lactone Anthelmintic Resistance in *Dirofilaria Immitis*", Topics in Companion Animal Medicine 26:4 (Nov. 2011) p. 186-192.
Bourguinat et al., "Macrocylic lactone resistance in *Dirofilaria immitis*", Veterinary Parasitology, 181:2 (Apr. 2011) p. 388-392.
Clark, Jeffrey, "Comment on the paper "Macrocyclic lactone resistance in *Dirofilaria immitis*" by Bourguinat et al.", Veterinary Parasitology 182:2-4 (Jun. 2011) p. 378-379.
Prichard, Roger, "Ivermectin resistance and overview of the Consortium for Anthelmintic Resistance SNPs", Expert Opinion on Drug Discovery, vol. 2, No. s1 (Oct. 2007) p. S41-S52.
Database EMBL [Online], "Wang-VSVGgfp-Jurkat-454-Avr-006514_1396 -1 300 Wang-VSVGgfp-Jurkat-454-Avr Homosapiens genomic, genomic survey sequence", XP002708500 retrieved from EBI accession No. EM_GSS:EI523 665 sequence (Apr. 2007).

* cited by examiner

```
1                G
  CGAAATCCAA AGATATTATT GCTTGATGAA GCGACCAGTG CATTAGATGC GGAAAGTGAA AGAGTTAGCT TTTTTAATTT TAAATTTTTA ATCTCTTGGA
                                                                                                              100
101
  ACTATTGAAT GATTTTTAAT TCACTATTCT TTTAGTCACG AAAAATTAGT TGGTTTCAAA AAATTCTATA ATTTTAAAAA GTCTTTCGCA GAGATTATTT
                                                                                                              200
201
  CATGTACAAT TTAATATCTT CATGAAAAAT TAGGATTAAT ATTTGTTAGG ATAAATCAGCT AAACTGAATA TAATCTAGCA AATTTTTTCA ATCATTAGAA
                                                                                                              300
301
  ATAAGGAACA TGAGGTAAAA AAATATGTGA ATATTGCGAA TACTTTTGAA TTGCCTTTTT TCTTAGTAAT TCTCATTATC ATAGTTTCAT TTCAGACAGT
                                                                                                              400
401
  TCAACAAGCT TTGGACGTTG CAAGTAGCGG TCGAACATGT ATTACAGTTG CACATAGACT ATCATCCATT CAGTTTGCAG ATCAGATATT TTTTGTAGAA
                                                                                                              500
501
  AATGGAAAAG TAGTTGAGCA GGGAACACAT CAAGAGCTCA TTGAATTGGA CGGGAAGTAC CTCGCAAACA AGATTTGAGG TCATAAATGG
                                                                                                              600
601         G
  TCAGAAATGA AGATAATATG GTA
                         623

Position 11 nucleotide A= amino acid K (lysine)
Position 11 nucleotide G= amino acid R (arginine)
```

MACROCYCLIC LACTONE RESISTANCE MARKER FOR *DIROFILARIA IMMITIS*

CROSS-REFERENCE TO RELATED APPLICATIONS

This application is a 371 application of PCT/CA2011/050169, filed Mar. 30, 2011, which claims the benefit of U.S. Provisional Application 61/319,982, filed Apr. 1, 2010, the contents of which are incorporated by reference herein.

FIELD OF THE INVENTION

The present invention relates to the detection of macrocyclic lactone resistant *Dirofilaria* spp.

BACKGROUND

Dirofilariasis is a parasitic disease of animals and occasionally in humans, which may result from infection by a species of *Dirofilaria* such as *D. immitis, D. repens, D. tenuis, D. ursi, D. subdermata, D. lutrae, D. striata* and *D spectans*.

*Dirofilaria immitis* (heartworm) is a parasitic nematode that commonly infects dogs, foxes, wolves, coyotes, and cats. Heartworms may cause serious vascular damage and may be fatal, especially in highly active animals.

The life cycle of *Dirofilaria immitis* is well known (reviewed in McCall et al., Adv Parasitol. 66:193-285, 2008). In brief, a mosquito may become infected when it draws blood from an infected host (e.g. a dog). In the mosquito, microfilariae develop to the infective larval stage. When the infected mosquito feeds, it may transmit larvae to a new host (e.g. another dog). In the new host the larvae continue to mature for eight to ten weeks, after which time they move to the right side of the lungs and the pulmonary artery, where they become adult. Adult worms mate and females produce eggs, which develop in utero into the long thin embryos (microfilariae) that are released into the bloodstream. A mosquito that takes in the circulating microfilariae when it draws blood from the infected host starts the cycle again.

*Dirofilaria immitis* may be found wherever its vector, the mosquito, is found. Generally, *Dirofilaria immitis* may be found on a world-wide basis, but are very common in areas with mild and warm climates.

Macrocyclic lactones are often prescribed as therapeutics or prophylactics in the management of *Dirofilaria immitis* in veterinary applications. However, resistance to macrocyclic lactones is common in a variety of parasitic nematodes and appears to be developing in *D. immitis*. A number of tests have been described for the detection of anthelmintic resistance in nematodes of livestock and horses, including, faecal egg count reduction test, the egg hatch test, microagar larval development test and molecular tests based on benzimidazole resistance (reviewed in Coles et al., Veterinary Parasitology 136: 167-185, 2006). Prichard et al. (European patent EP 0979278) describes a P-glycoprotein sequence in *Haemonchus contortus* which may be useful for the diagnosis of macrocyclic lactone resistance in parasitic nematodes. However, there remains a need for methods to detect *Dirofilaria immitis* (heartworms) that are resistant to a macrocyclic lactone.

SUMMARY OF THE INVENTION

In one aspect, the invention relates to a method for determining the responsiveness of a *Dirofilaria* spp. nematode to a macrocyclic lactone, said method comprising determining the genotype of said nematode at a position in a P-glycoprotein gene of said nematode corresponding to position 11 in SEQ ID NO: 1. The method may further comprise the step of determining the genotype of said nematode at a position in said P-glycoprotein gene of said nematode corresponding to position 618 in SEQ ID NO: 1. A determination that the nematode has the genotype GG at a position corresponding to position 11 in SEQ ID NO: 1 or has the genotype GG at positions corresponding to positions 11 and 618 in SEQ ID NO: 1 indicates that the nematode is likely to be resistant to said macrocyclic lactone.

In another aspect, the invention relates to an isolated nucleic acid molecule possessing at least 80% sequence identity to SEQ ID NO: 1 over its entire length and comprising the nucleotide guanine (G) at a position corresponding to position 11 of SEQ ID NO: 1, or a fragment of said nucleic acid molecule having a length of at least 50 nucleotides and containing said G nucleotide at a position corresponding to position 11 of SEQ ID NO: 1. The isolated nucleic acid molecule may further comprise the nucleotide guanine (G) at a position corresponding to position 618 of SEQ ID NO: 1, or a fragment of said nucleic acid molecule having a length of at least 50 nucleotides and containing said G nucleotide at a position corresponding to position 618 of SEQ ID NO: 1.

In another aspect, the invention relates to a kit for determining the responsiveness of a *Dirofilaria* spp. nematode to a macrocyclic lactone, the kit comprising: a probe capable of determining the genotype of the *Dirofilaria* spp. nematode at a position in a P-glycoprotein gene of the nematode corresponding to position 11 of SEQ ID NO: 1; or a probe capable of determining the genotype of the *Dirofilaria* spp. nematode at positions in a P-glycoprotein gene of the nematode corresponding to positions 11 and 618 of SEQ ID NO: 1.

In another aspect, the invention relates to a method for selecting a treatment to treat an animal infected with a *Dirofilaria* spp. nematode, the method comprising determining the genotype of said nematode at a position in a P-glycoprotein gene of said nematode corresponding to position 11 in SEQ ID NO: 1, and selecting the treatment based on the genotype of said nematode. This method may further comprise the steps of determining the genotype of said nematode at a position in the P-glycoprotein gene of said nematode corresponding to position 618 in SEQ ID NO: 1 and/or of treating the animal with the selected treatment, wherein the treatment is an arsenic-based therapy, diethylcarbamazine, antibiotics, or a combination of one or more thereof, if the nematode has the genotype GG at a position in the P-glycoprotein gene of the nematode corresponding to position 11 in SEQ ID NO: 1; or if the nematode has the genotype GG at positions in the P-glycoprotein gene of said nematode corresponding to positions 11 and 618 in SEQ ID NO: 1.

In another aspect, the invention relates to a method for selecting a prophylactic to prevent an animal from becoming infected by a *Dirofilaria* spp. nematode, the method comprising determining the genotype of said nematode at a position in a P-glycoprotein gene of said nematode corresponding to position 11 in SEQ ID NO: 1, and selecting the prophylactic based on the genotype of said nematode. This method may further comprise the steps of determining the genotype of said nematode at a position in the P-glycoprotein gene of said nematode corresponding to position 618 in SEQ ID NO: 1 and/or of providing the animal with the selected prophylactic, wherein the prophylactic is diethylcarbamazine, if the nematode has the genotype GG at a position in the P-glycoprotein gene of the nematode corresponding to position 11 in SEQ ID NO: 1; or if the nematode has the genotype GG at positions in the P-glycoprotein gene of the nematode corresponding to positions 11 and 618 in SEQ ID NO: 1.

In a further aspect, the invention relates to an isolated nucleic acid molecule comprising the sequence depicted in SEQ ID NO: 1.

Methods of the invention may further comprise steps of obtaining a sample comprising the nematode from a subject such as an animal, isolating the nematode from the sample, isolating nucleic acids from the nematode, and optionally purifying the nucleic acids prior to the step of determining the genotype of the nematode. Moreover, the genotype of the nematode may be determined using known techniques, such as, DNA sequencing, hybridization with allele specific oligonucleotides, single strand conformational polymorphism (SSCP), microarray analysis or approaches based on PCR, RT-PCR or qRT-PCR.

Other aspects, advantages and features of the present invention will become apparent to those of ordinary skill in the art upon review of the following description of specific embodiments of the invention in conjunction with the accompanying figures.

BRIEF DESCRIPTION OF THE DRAWINGS

FIG. 1: A nucleotide sequence comprising a partial coding sequence for P-glycoprotein (SEQ ID NO: 1). The SNPs are indicated in bold.

DETAILED DESCRIPTION

Figure 2:
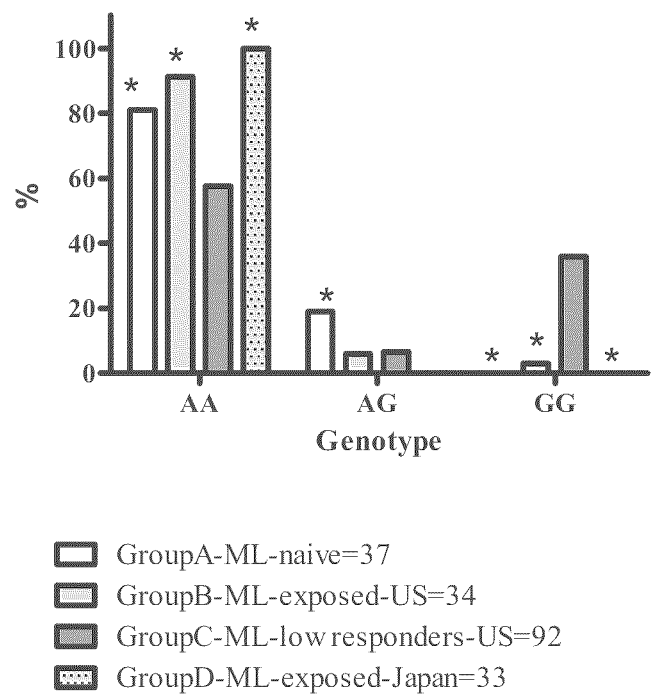
FIG. 2: Genotype frequency of SNP at position 11 of P-glycoprotein gene (*=p-value significant).

Macrocyclic lactones, including but not limited to avermectins and milbemycins, are products, or chemical derivatives thereof, of soil microorganisms that belong to the genus *Streptomyces*. These molecules are widely used to treat hundreds of species of endo- and ectoparasites in a wide range of hosts. Avermectins in commercial use include, without limitation, ivermectin, abamectin, doramectin, eprinomectin and selamectin. Commercially available milbemycins include, without limitation, milbemycin oxime and moxidectin. Macrocyclic lactones have a potent, broad antiparasitic spectrum at low dose levels. They are active against many immature nematodes (including hypobiotic larvae) and arthropods. A single therapeutic dose may persist in concentrations sufficient to be effective against incumbent nematode infections for prolonged periods after treatment.

Macrocyclic lactone (ML) heartworm preventatives were developed for the treatment of dogs and cats, which were not already infected, to prevent establishment of adult infections by targeting the developing L3/L4 stages. Macrocyclic lactones also have effects on the microfilarial stage (L1) (Bowman et al., 1992; Courtney et al., 1998; McCall et al., 1998). Macrocyclic lactone endectocides such as ivermectin (IVM), milbemycin oxime (MBO), moxidectin (MOX) and selamectin (SLM) are used during the transmission season for chemoprophylaxis for heartworm in dogs and cats. However, in recent years, some experts have suggested that macrocyclic lactones could be used monthly to suppress reproduction in adult worms and remove microfilarial (mf) stages, thereby reducing transmission and gradually causing the attrition of adult worms. It would not be necessary to only treat animals without an established adult infection in order to prevent infection and gradually remove an existing infection—the "safety net story about macrocyclic lactone heartworm preventives" (McCall, 2005).

While the developing L3/L4 stages of *D. immitis* are ultra sensitive to macrocyclic lactones, it appears that macrocyclic lactones cause a cumulative insult which affects the ability of adults to reproduce and can eventually be lethal to both adults and microfilaria. However, it is not known how the macrocyclic lactones act on the different stages of this parasite. The classical view is that macrocyclic lactones act by opening glutamate- or GABA-gated chloride channels, which leads to paralysis of the pharynx and/or the body muscles, resulting in starvation or an inability of the nematodes to move, which is lethal for parasites in the gastrointestinal tract. These effects are based on observations in *Caenorhabditis elegans* and trichostrongylid nematode parasites, are relatively acute, and lead to fairly rapid paralysis and death. In filarial nematodes such as *D. immitis*, these rapid effects do not occur, at least not in adults and microfilariae, and repeated treatments are required to produce lethality. IVM does not paralyze adult filariae or microfilariae in vitro (Bennett, Williams & Dave, 1988) and it is believed that in the filarial nematodes the pharynx is vestigial and that nutrient uptake occurs through the cuticle (Stote, Bonow & Attah, 1996).

There is much evidence of macrocyclic lactone resistance in nematode parasites of ruminants (for reviews see Kaplan, 2004; Wolstenholme et al., 2004; Geary, 2005) and recently there have been reports of IVM resistance in nematode parasites of horses (Boersema, Eysker & Nas, 2002; Hearn & Peregrine, 2003), including *Cyathostomum* species (Trawford, Burden & Hodgkinson, 2005; Molento, pers. comm.) and in the human filarial nematode *Onchocerca volvulus* (Osei-Atweneboana et al., 2007). Unfortunately, there is some evidence now (Hampshire, 2005) that there has been a loss of efficacy of macrocyclic lactone heartworm preventatives, against *D. immitis*, in some locations in recent years.

When macrocyclic lactone-resistant trichostrongylid parasites, such as *Haemonchus contortus* and *Cooperia oncophora*, have been compared with macrocyclic lactone susceptible isolates, genetic changes in glutamate-gated chloride channel (GluCl) subunits (Blackhall et al., 1998a; Njue et al., 2004), a GABA-gated chloride channel (GABA-Cl) subunit (Feng et al., 2002; Blackhall et al., 2003), P-glycoprotein (Pgp) ABC transporters (Blackhall et al., 1998b; Xu et al., 1998; Le Jambre et al., 1999; Sangster et al., 1999) and in β-tubulin (Eng et al., 2006; Mottier & Prichard, 2008) have been reported. In the free-living nematode *C. elegans*, the deletion of three GluCl subunits resulted in a high level loss of susceptibility to IVM (Dent et al., 2000), indicating that these GluCls are involved in the action of IVM on this nematode. However, this cannot be interpreted to imply that macrocyclic lactone resistance mechanisms in parasitic nematodes necessarily involve changes in GluCls.

As noted above, IVM resistance (Osei-Atweneboana et al., 2007) and sub-optimal responses to IVM (Ali et al., 2002; Awadzi et al., 2004a, 2004b) have now been reported in the human filarial parasite *O. volvulus*. It should be noted that *O. volvulus* is phylogenetically much closer to *D. immitis* than are the trichostrongylid parasites or *C. elegans*. Extensive investigations have been made into genetic changes that may be associated with a developing IVM resistance in *O. volvulus*. Eng & Prichard (2005) investigated a large number of candidate and non-candidate genes for association with IVM resistance in *O. volvulus*. No evidence was found for selection on GluCl or GABA-Cl genes, but significant selection on β-tubulin and P-glycoprotein gene were observed. Further investigations have confirmed selection on β-tubulin (Eng et al., 2006; Bourguinat et al., 2007), on P-glycoprotein gene, and on other ABC transporter genes in *O. volvulus* (Ardelli & Prichard, 2004; Ardelli & Prichard, 2007; Ardelli et al., 2005; 2006a; 2006b; Bourguinat et al., 2008). Single nucleotide polymorphisms (SNPs) for IVM selection have been identified for *O. volvulus* in β-tubulin (Eng et al., 2006) and a half-sized ABC transporter, OvPLP (Bourguinat et al., 2008) and may be useful markers for monitoring for macrocyclic lactone resistance in this filarial nematode.

The loss of efficacy of macrocyclic lactone heartworm preventatives could have a genetic basis and indicate a developing drug resistance situation in *Dirofilaria immitis*. IVM is a substrate of P-glycoprotein (Lespine et al. 2009) and P-glycoprotein has been shown to be implicated in resistance to avermectin anthelminthics (Xu et al. 1998).

The present invention relates to methods and kits for determining the responsiveness of a *Dirofilaria* spp. nematode to a macrocyclic lactone and to an isolated nucleic acid molecule of said nematode.

Nucleic Acid Molecule

In one aspect, the invention relates to an isolated nucleic acid molecule possessing at least 80% sequence identity to SEQ ID NO: 1 over its entire length and comprising the nucleotide guanine (G) at a position corresponding to position 11 of SEQ ID NO: 1, or a fragment of said nucleic acid molecule having a length of at least 50 nucleotides and containing said G nucleotide at a position corresponding to position 11 of SEQ ID NO: 1.

In one embodiment of the invention, the isolated nucleic acid molecule may further comprise the nucleotide guanine (G) at a position corresponding to position 618 of SEQ ID NO: 1, or a fragment of said nucleic acid molecule having a length of at least 50 nucleotides and containing said G nucleotide at a position corresponding to position 618 of SEQ ID NO: 1.

In another aspect, the invention relates to an isolated nucleic acid molecule comprising, consisting of, or consisting essentially of the sequence depicted in SEQ ID NO: 1.

As used herein, "nucleic acid", "nucleotide sequence" or "nucleic acid molecule" may refer to a polymer of DNA and/or RNA which may be single or double stranded and optionally containing synthetic, non-natural or altered nucleotide bases capable of incorporation into DNA or RNA polymers. "Nucleic acids", "Nucleic acid sequences" or "Nucleic acid molecules" may encompass genes, cDNA, DNA (e.g. genomic DNA) and RNA encoded by a gene. Nucleic acids or nucleic acid sequences may comprise at least 3, at least 10, at least 100, at least 1000, at least 5000, or at least 10000 nucleotides or base pairs.

"Nucleic acids", "Nucleic acid sequences" or "Nucleic acid molecules" may be modified by any chemical and/or biological means known in the art including, but not limited to, reaction with any known chemicals such as alkylating agents, browning sugars, etc; conjugation to a linking group (e.g. PEG); methylation; oxidation; ionizing radiation; or the action of chemical carcinogens. Such nucleic acid modifications may occur during synthesis or processing or following treatment with chemical reagents known in the art.

As used herein, "consists essentially of" or "consisting essentially of" means that the nucleic acid sequence may include one or more nucleotide bases, including within the sequence or at one or both ends of the sequence, but that the additional nucleotide bases do not materially affect the function of the nucleic acid sequence.

A nucleic acid molecule of the invention may comprise a sequence corresponding to that of SEQ ID NO: 1 over its length. In embodiments of the invention, the nucleic acid sequence may be at least about 80%, at least about 81%, at least about 82%, at least about 83%, at least about 84%, at least about 85%, at least about 86%, at least about 87%, at least about 88%, at least about 89%, at least about 90%, at least about 91%, at least about 91%, at least about 92%, at least about 93%, at least about 94%, at least about 95%, at least about 96%, at least about 97%, at least about 98%, at least about 99% or 100% identical to SEQ ID NO: 1, but that was isolated from a nematode having the genotype GG at a position corresponding to position 11 of SEQ ID NO: 1 or at positions corresponding to positions 11 and 618 of SEQ ID NO: 1.

An "isolated nucleic acid molecule" may refer to a nucleic acid molecule that does not occur in nature as part of a larger polynucleotide sequence; and/or may be substantially free from any other nucleic acid molecules or other contaminants that are found in its natural environment. As used herein, an "isolated nucleic acid molecule" may also encompass recombinantly or synthetically produced nucleic acid molecules.

The term "identity" or "identical" refers to sequence similarity between two polypeptide or polynucleotide molecules. Identity can be determined by comparing each position in the aligned sequences. A degree of identity between amino acid or nucleic acid sequences is a function of the number of identical or matching amino acids or nucleic acids at positions shared by the sequences, for example, over a specified region. Optimal alignment of sequences for comparisons of identity may be conducted using a variety of algorithms, as are known in the art, including the Clustal W™ program, available at http://clustalw.genome.ad.jp, the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm (e.g. BLASTn and BLASTp), described in Altschul et al., 1990, J. Mol. Biol. 215:403-10 (using the published default settings). Software for performing BLAST analysis is available through the National Center for Biotechnology Information. In one aspect, two sequences may be aligned using the "Blast 2 Sequences" tool at the NCBI website at default settings (Tatusova and Madden. FEMS Microbiol Lett, 174: 247-250, 1999). In another embodiment, the person skilled in the art can readily and properly align any given sequence and deduce sequence identity/homology by mere visual inspection.

A nucleic acid molecule of the invention may be derived from a *Dirofilaria immitis* nematode with the genotype GG in P-glycoprotein at positions corresponding to position 11 or at positions 11 and 618 of SEQ ID NO: 1. As used herein, "derived from" may refer to a nucleic acid molecule that was isolated from a natural source, e.g. a *Dirofilaria immitis* nematode. It may also refer to a nucleic acid molecule that is man-made, e.g. recombinantly or synthesized on the basis of a nucleic acid molecule isolated from a *Dirofilaria immitis* nematode.

As used herein, "genotype" refers to the genetic constitution of a cell, an organism, or an individual (i.e. the specific allele makeup of the individual) usually with reference to a specific character under consideration. In the context of the invention, e.g. a GG genotype may mean that at a specific position of a gene which has two alleles, the nucleotide at the same location in each allele is G (guanine). Alleles are alternative DNA sequences at the same physical locus, which may or may not result in different phenotypic traits. In any particular diploid organism, with two copies of each chromosome, the genotype for each gene comprises the pair of alleles present at that locus, which are the same in homozygotes and different in heterozygotes.

Genetic analysis provided herein linked macrocyclic lactone resistance with a polymorphic variant of P-glycoprotein. As used herein, the term "polymorphic site" refers to a region in a nucleic acid at which two or more alternative nucleotide sequences are observed in a significant number of nucleic acid samples from a population of individuals. A polymorphic site that is one nucleotide in length may be referred to herein as a "single nucleotide polymorphism" or a "SNP."

The sequence depicted in SEQ ID NO: 1 encodes a portion of P-glycoprotein from *Dirofilaria immitis*. P-glycoprotein was first cloned from Chinese hamster ovary cells and characterized on the basis of its ability to confer a multidrug resistance phenotype to cancer cells that had developed resistance to chemotherapy drugs [Juliano et al. Biochim. Biophys. Acta 455 (1): 152-62, 1976].

P-glycoprotein is extensively distributed and may be expressed, for example, in the intestinal epithelium, hepatocytes, renal proximal tubular cells, adrenal gland and capillary endothelial cells comprising the blood-brain and blood-testis barrier.

P-glycoprotein is a member of the superfamily of ATP-binding cassette (ABC) transporters. Specifically, P-glycoprotein is a member of the MDR/TAP subfamily, which are involved in multidrug resistance. P-glycoprotein is an ATP-dependent drug efflux pump for xenobiotic compounds with broad substrate specificity. It may be responsible for decreased drug accumulation in multidrug-resistant cells and often mediates the development of resistance to drugs.

A skilled person would appreciate that a nucleic acid molecule derived from a *Dirofilaria immitis* nematode with the genotype GG at a position in P-glycoprotein corresponding to position 11 of SEQ ID NO: 1, or from a *Dirofilaria immitis* nematode with the genotype GG at positions in P-glycoprotein corresponding to positions 11 and 618 of SEQ ID NO: 1 may encode a P-glycoprotein that differs from that of a macrocyclic lactone sensitive nematode. For example, such a P-glycoprotein may have at least one amino acid modification. A non-limiting amino acid modification may include an amino acid substitution. In one embodiment, the amino acid substitution may be a conservative substitution. As used herein, the term "conservative substitution" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Specific, non-limiting examples of a conservative substitution include the following:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In another embodiment, the at least one amino acid modification may be a substitution modification that affects the function of P-glycoprotein. For example, *Dirofilaria immitis* expressing the modified P-glycoprotein may be, for example, resistant or sensitive to a macrocyclic lactone.

In further embodiments, the altered P-glycoprotein may be a marker for a macrocyclic lactone resistant *Dirofilaria immitis* nematode; or may contribute to macrocyclic lactone resistance in a *Dirofilaria immitis* nematode.

Methods of Determining Responsiveness of *D. immitis* to a Macrocyclic Lactone

In another aspect, the present invention relates to a method for determining the responsiveness of a *Dirofilaria* spp. nematode to a macrocyclic lactone, said method comprising determining the genotype of said nematode at a position in a P-glycoprotein gene of said nematode corresponding to position 11 in SEQ ID NO: 1.

In an embodiment of the invention, the method may further comprise determining the genotype of said nematode at a position in said P-glycoprotein gene of said nematode corresponding to position 618 in SEQ ID NO: 1.

In the context of the invention, a nematode is likely to be resistant to said macrocyclic lactone if the nematode has the genotype GG at a position in P-glycoprotein corresponding to position 11 in SEQ ID NO: 1. In one aspect, a nematode is likely to be resistant to said macrocyclic lactone if the nematode has the genotype GG at positions in P-glycoprotein corresponding to positions 11 and 618 in SEQ ID NO: 1.

As used herein, the term "responsiveness" may mean that the nematode responds following exposure to a macrocyclic lactone. In embodiments of the invention, a nematode may respond by being sensitive or resistant to a macrocyclic lactone. Sensitivity to a macrocyclic lactone means that the macrocyclic lactone adversely affects the exposed *Dirofilaria immitis* nematode. For example, a macrocyclic lactone may be lethal or sub-lethal to the *Dirofilaria immitis* nematode, or shorten its life-span. Resistance is the reduction in effectiveness of a drug in curing a disease or improving a patient's symptoms. A *Dirofilaria immitis* nematode may be macrocyclic lactone resistant if the drug meant to neutralize it is ineffective. A *Dirofilaria immitis* nematode may also be macrocyclic lactone resistant if the drug, at a specific dose that is meant to neutralize it, has reduced effect.

In embodiments of the invention, responsiveness of a nematode to a macrocyclic lactone may be determined in vivo or in vitro.

In one embodiment, a *Dirofilaria immitis* nematode may be said to be resistant to a macrocyclic lactone if less than about 93%, less than about 91%, less than about 89%, less than about 87%, less than about 85%, less than about 83%, less than about 81%, less than about 79%, less than about 77%, less than about 75%, less than about 73%, less than about 71%, less than about 69%, less than about 67%, less than about 65%, less than about, 63%, less than about 61%, less than about 59%, less than about 57%, less than about 55%, less than about 53%, less than about 51%, less than about 49%, less than about 47%, less than about 45%, less than about 43%, less than about 41%, less than about 39%, less than about 37%, less than about 35%, less than about 33%, less than about 31%, less than about 29%, less than about 27%, less than about 25%, less than about 23%, less than about 21%, less than about 19%, less than about 17%, less than about 15%, less than about 13%, less than about 11%, less than about 9%, less than about 7%, less than about 5%, less than about 3%, less than about 1% or if 0% of nematodes died following exposure to a LD95 (a lethal dose or concentration of a drug that should have killed 95% of *Dirofilaria immitis* nematodes) dose or concentration of a macrocyclic lactone.

In another embodiment, a *Dirofilaria immitis* nematode may be said to be sensitive to a macrocyclic lactone if at most about 5%, at most about 4%, at most about 3%, at most about 2%, at most about 1% or if 0% of nematodes survived following exposure to a LD95 (a lethal dose or concentration of a drug that should have killed 95% of *Dirofilaria immitis* nematodes) dose or concentration of a macrocyclic lactone.

Contacting the Nucleic Acid Sample with a Probe

A biological sample comprising a *Dirofilaria immitis* nematode may be obtained from a subject. The subject may be, without limitation, a dog, fox, wolf, coyote or cat. In the context of the invention, a biological sample may be any sample (e.g. bodily fluid, excrement, organ, tissue, etc) from a subject. The biological sample may be from a subject that is known to have, or is suspected of having, a *Dirofilaria immitis* nematode infection. The *Dirofilaria immitis* nematode may be isolated from the biological sample with standard separation methods and techniques.

A nucleic acid sample may be isolated or obtained from a *Dirofilaria immitis* nematode prior to use. Methods of isolating nucleic acids from organisms and tissues are known. Such methods may include, but are not limited to, traditional DNA extraction, with proteinase K digestion followed by phenol chloroform extraction, sodium hydroxide extraction, and physical disruption, followed by purification, e.g. by cesium chloride centrifugation or high performance liquid chromatography (HPLC); or the use of commercial kits, e.g. QIAamp™ or DNeasy™. A skilled person would appreciate that different approaches may be used to isolate a nucleic acid sample from an adult *Dirofilaria immitis* nematode in comparison to a microfilaria. In an embodiment of the invention, the nucleic acid sample comprises genomic DNA.

A nucleic acid sample may be contacted with a probe to determine the genotype of a nematode at one or more positions in P-glycoprotein. A suitable incubation medium and incubation conditions may be used to incubate the probe and the sample. In one embodiment, the probe and the nucleic acid sample may be incubated in any medium that allows the probe and the nucleic acid sample to interact, for example by contact. For example, the incubation medium may be a buffer, such as PBS. A skilled person would appreciate that the composition of the incubation medium may depend on the probe used and/or the constituents of the nucleic acid sample.

Probe

Methods and kits of the invention may comprise a probe to detect the genotype of the nematode at a position in P-glycoprotein. A probe of the invention may be used to determine the genotype of the nematode at a position in P-glycoprotein corresponding to position 11 of SEQ ID NO: 1. In one embodiment of the invention, a probe may be used to simultaneously or serially determine the genotype of the nematode at positions in P-glycoprotein corresponding to positions 11 and 618 of SEQ ID NO: 1.

A probe of the invention may be one or more molecules that are capable of binding to, or associating with, the nucleic acid sample to determine the genotype of the nematode at one or more specific positions in P-glycoprotein. In this regard, the probe may be, for example, an oligonucleotide, a primer, an aptamer or an antibody.

An oligonucleotide of the invention is capable of determining the genotype of a nematode at a position in P-glycoprotein corresponding to position 11 of SEQ ID NO: 1 or at positions corresponding to position 11 and 618 of SEQ ID NO: 1, in an allele specific manner. An oligonucleotide may comprise any size, shape and composition that is suitable for use in the context of the invention. Preferably, an oligonucleotide of the invention may comprise DNA, RNA, synthetic nucleotides, non-natural nucleotides, altered nucleotides, or combinations of one or more thereof. In one embodiment, an oligonucleotide of the invention may comprise locked nucleic acids and/or peptide nucleic acids.

An oligonucleotide may be of any length that is suitable for use in methods of the invention. Generally, an oligonucleotide that is capable of detecting the genotype of a nematode at one position does not interfere with the detection at the other. However, an oligonucleotide of the invention may be capable of simultaneously detecting the genotype of a nematode at two positions in P-glycoprotein (e.g. at positions corresponding to positions 11 and 618 of SEQ ID NO: 1). In embodiments of the invention, an oligonucleotide may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, or more nucleotides.

In embodiments of the invention, an oligonucleotide may encompass, without limitation, a primer or more than one primer, e.g. a primer pair, such as a forward primer and a reverse primer.

A primer may be an oligonucleotide that may be used to initiate DNA replication. Typically, a primer is a short oligonucleotide that may be about 10, about 15, about 20, about 25, about 30, about 35, about 40, about 45, about 50, about 55, about 60, about 65, about 70, about 75, about 80, about 85, about 90, about 95, about 100 or more nucleotides.

A primer may be used as part of an approach to detect the genotype of a nematode at a specific location of a gene. For example, a primer may be useful in amplifying DNA such as by PCR, RT-PCR and qRT-PCR, for subsequent analysis, such as by Southern blot, sequencing or SSCP.

As used herein, an "aptamer" may be a nucleic acid or a peptide molecule that binds to a specific molecular target. For example, in solution, a chain of nucleotides may form intramolecular interactions that fold the aptamer into a complex three-dimensional shape. The shape of that aptamer allows it to bind tightly against the surface of its target molecule. Because of the diversity of molecular shapes that exists for nucleotide and amino acid sequences, aptamers may be obtained for a wide array of molecular targets, including, but not limited to, nucleic acid molecules, enzymes, membrane proteins, viral proteins, cytokines, growth factors, and immunoglobulins.

An aptamer of the invention may be a nucleic acid molecule. Said aptamer may comprise DNA, RNA, synthetic nucleotides, non-natural nucleotides, altered nucleotides, or combinations of one or more thereof. The nucleic acid aptamer may be single-stranded or double-stranded. A nucleic acid aptamer may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 500, or more nucleotides. A preferred nucleic acid aptamer may be a single stranded nucleic acid molecule and comprise a sequence of less than about 100 nucleotides.

An aptamer of the invention may be a peptide molecule. A peptide aptamer may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200 or more amino acid residues. A preferred peptide aptamer may comprise a sequence of between about 15 to about 75 amino acid residues.

As used herein, the terms "peptide", "oligopeptide", "polypeptide" and "protein" may be used interchangeably and may encompasses any chain of naturally or non-naturally occurring amino acids (either D- or L-amino acids), regardless of length (e.g., at least 5, 6, 8, 10, 12, 14, 16, 18, 20, 25, 30, 40, 50, 100 or more amino acids) or post-translational modification (e.g., glycosylation or phosphorylation) or the presence of e.g. one or more non-amino acyl groups (for example, sugar, lipid, etc.) covalently linked to the peptide, and includes, for example, natural proteins, synthetic or recombinant polypeptides and peptides, hybrid molecules, peptoids, peptidomimetics, etc. Peptides may also be monomeric or multimeric. Peptide fragments may comprise a contiguous span of at least 5, at least 10, at least 25, at least 50, at least 100, at least 250, at least 500, at least 1000, at least 1500, or at least 2500 consecutive amino acids and may retain the desired activity of the full length peptide.

As used herein, an "antibody" may include monoclonal antibodies (including full length monoclonal antibodies), polyclonal antibodies, multispecific antibodies (e.g., bispecific antibodies), single domain antibodies and antibody fragments. "Antibody fragments" comprise a portion of a full length antibody, generally the antigen binding or variable region thereof. Examples of antibody fragments include, but are not limited to, Fab, Fab', F(ab')2, and Fv fragments; diabodies; linear antibodies; single-chain antibody molecules; and multi-specific antibodies formed from antibody fragments. The term "antibody" may also include chimeric or humanized antibodies.

A probe of the invention may be prepared according to standard techniques known to a skilled person. For example, a probe may be produced synthetically, recombinantly or may be isolated from a natural source. In one embodiment, the source may be a biological source, for example, from a microorganism (e.g. a bacteria or a virus), an animal (e.g. a mouse, a rat, a rabbit, a goat, or a human), or a plant.

In the context of the invention, "a probe" may mean one probe or more than one probe. In one embodiment, a single probe may be used to detect the genotype of a nematode at positions in P-glycoprotein corresponding to positions 11 and 618 of SEQ ID NO: 1. A skilled person would appreciate that one or more probes may be useful in the context of the invention and may depend on the genotyping approach taken. For example, a primer is often used in pairs, i.e. a forward primer and a reverse primer, in amplification reactions. The amplified products may be subsequently analyzed to identify the nucleotide at a specific location.

One or more types of probes may be simultaneously used in methods of the invention. In one embodiment two probes of different types may be used to simultaneously detect in a sequence from a nematode positions corresponding to positions 11 and 618 of SEQ ID NO: 1. For instance, one probe may be an oligonucleotide to detect a nucleotide at a position corresponding to position 11 of SEQ ID NO: 1; and another probe may be an antibody to detect the nucleotide at a position corresponding to position 618 of SEQ ID NO: 1. In another embodiment, the two probes may comprise the same type of molecule.

Probe design and production are known in the art. Generally, a probe may be produced recombinantly, synthetically, or isolated from a natural source, e.g. from a cell, an animal or a plant. However, a skilled person would appreciate that probe production may depend on the type of probe at issue.

A skilled person would appreciate that a probe of the invention may need to be able to differentiate between the GG/GG genotype (i.e. a nematode having a GG genotype at positions in P-glycoprotein corresponding to positions 11 and 618 of SEQ ID NO: 1) from the other possible genotypes, e.g. AA/AA, AG/AA AG/AG . . . AA/AG, etc. A preferred probe may be a nucleic acid molecule (e.g. a primer), with or without a fluoroflor or dye. A probe may be linear or in the form of a hairpin, with a fluoroflor, with or without a quencher or another fluoroflor (e.g. for FRET analysis). It could also be an antibody that specifically recognizes the DNA (or protein) sequence. Another probe could be based on a RNA molecule. What would be preferred may depend on technical considerations, stability, cost, ease of use, etc.

Determining Genotype

A skilled person would understand that routine approaches may be used to determine the genotype of a nematode at one or more position in P-glycoprotein. Suitable approaches for use in the context of the invention may include, without limitation, PCR, RT-PCR, qRT-PCR, SSCP, hybridization with allele specific oligonucleotides and the use of antibodies to determine the genotype of a nematode at a position in P-glycoprotein corresponding to position 11 of SEQ ID NO: 1 or to determine the genotype of a nematode at positions in P-glycoprotein corresponding to positions 11 and 618 of SEQ ID NO: 1. Other approaches may include nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA).

Polymerase chain reaction (PCR) (U.S. Pat. Nos. 4,683, 195; 4,683,202; and 4,965,188) is a process that is used to increase the concentration of a target nucleic acid sequence in a sample. The method typically involves the use of forward and reverse primers that are complementary to the target sequence to amplify the target sequence; and a cycle of three temperatures to promote denaturation, annealing and extension.

Quantitative RT-PCR is used to quantify mRNA in both relative and absolute terms. Real time PCR is based on the principle of PCR but allows the reliable detection and quantification of nucleic acid sequences. PCR reactions may be divided into three segments: an exponential phase, a linear phase and a plateau phase. Theoretically, during the exponential phase, there is a quantitative relationship between the amount of starting target sequence and the amount of PCR product at any given cycle. Within the exponential phase, a real-time PCR instrument calculates two values. The Threshold line is the level of detection at which a reaction reaches a fluorescent intensity above background. The PCR cycle at which the sample reaches this level is called the Cycle Threshold, Ct. The Ct value is used in quantitation or presence/absence detection analysis. By comparing the Ct values of samples of unknown concentration with a series of standards, the amount of template DNA in an unknown reaction can be accurately determined.

Real time PCR relies on the nuclease activity of the polymerase and the use of a reporter molecule that binds to the amplification product. Common reporter molecules include, without limitation, (1) the use of fluorescent dyes that intercalate with double-stranded DNA, and (2) modified DNA oligonucleotide probes that fluoresce when hybridized with a complementary DNA. For example, the reporter molecule may comprise a labeled oligonucleotide that binds a target to be amplified (template). The labeled oligonucleotide may comprise a fluorescent molecule at one end and a quenching molecule at the other, which quenches the fluorescence of the fluorescent molecule. As the polymerase traverses the template, it will reach and cleave the fluorescent molecule from the labeled oligonucleotide. The fluorescence of the cleaved fluorescent molecule may be detected. The amount of fluorescence is directly proportional to the amount of template/per product produced.

The amplified nucleic acid molecules may be used in conjunction with approaches to determine the genotype of a nematode with respect to P-glycoprotein. Such approaches may include, without limitation, DNA sequencing, hybridization with allele specific oligonucleotides, southern blot analysis, and SSCP.

Single-strand conformation polymorphism (SSCP) technique is a simple and efficient means to detect any small alteration in PCR-amplified product. It is based on the assumption that subtle nucleic acid change affects the migration of single-stranded DNA fragment and, therefore, results in visible mobility shifts across a nondenaturing polyacrylamide gel (Orita, M., Iwahana, H., Kanazawa, H., Hayashi, K., and Sekiya, T. Detection of polymorphism of human DNA by gel electrophoresis as single-strand conformation polymorphisms. Proc. Natl. Acad. Sci. USA 86, 2766-2770 (1989)).

Hybridization with allele specific oligonucleotides. An allele-specific oligonucleotide (ASO) is a short piece of synthetic DNA complementary to the sequence of a variable target DNA. It may act as a probe to detect for the presence of the target in a Southern blot assay or in a Dot blot assay. An ASO is typically an oligonucleotide of 15-21 nucleotide bases in length. It is designed to be specific for only one version, or allele, of the DNA being tested. The length of the ASO, which strand it is chosen from, and the conditions by which it is bound to (and washed from) the target DNA all play a role in its specificity. These probes can usually be designed to detect a difference of as little as 1 base in the target's genetic sequence, a basic ability in the assay of single-nucleotide polymorphisms (SNPs). To be detected after it has bound to its target, the ASO may be labeled with a radioactive, enzymatic, or fluorescent tag. For example, the Illumina Methylation Assay technology takes advantage of ASO to detect one base pair difference (cytosine versus thymine) to measure methylation at a specific CpG site. PCR may be paired with ASO analysis [Saiki et al. Nature 324(6093): 163-166, 1986].

Direct DNA sequencing and Restriction Fragment Length Polymorphism (RFLP) based techniques are widely known. RFLP is a technique for analyzing the variable lengths of DNA fragments that result from digesting a DNA sample with a restriction endonuclease, followed by Southern blot analysis. The resultant pattern may be used in the detection of polymorphisms. DNA sequencing refers to generally to methods for determining the order of the nucleotide bases—adenine, guanine, cytosine, and thymine—in a molecule of DNA.

Other suitable methods of genotyping may include, without limitation, microarray analysis, SmartAmp2 amplification, pyrosequencing, mass spectrometry, molecular beacons, and ELISA (e.g. dipstick ELISA). A DNA microarray is a multiplex technology used in molecular biology and in medicine. It consists of an arrayed series of thousands of microscopic spots of DNA oligonucleotides, each containing picomoles (10-12 moles) of a specific DNA sequence (probes). DNA microarrays can be used to measure changes in expression levels, to detect single nucleotide polymorphisms (SNPs), to genotype or re-sequence mutant genomes (see uses and types section) of a given sample.

Position 11 of SEQ ID NO: 1 is within an exon of P-glycoprotein and position 618 of SEQ ID NO: 1 corresponds to a non-coding region. A macrocyclic lactone resistant *D. immitis* has the genotype GG at a position in P-glycoprotein corresponding to position 11 or to positions 11 and 618 of SEQ ID NO: 1. Thus, a P-glycoprotein expressed in a macrocyclic lactone resistant *D. immitis* nematode may have an altered amino acid sequence that may be useful to indirectly detect the GG genotype of a nematode at a position in P-glycoprotein corresponding to position 11 of SEQ ID NO: 1. In an embodiment of the invention, an antibody that is capable of detecting an amino acid sequence encoded by a nucleic acid sequence which comprises guanine at a position corresponding to position 11 of SEQ ID NO: 1 may be useful in detecting the GG genotype of a nematode with respect to P-glycoprotein.

Once a *Dirofilaria immitis* nematode with the genotype GG at a position in P-glycoprotein corresponding to position 11 of SEQ ID NO: 1, or at positions corresponding to positions 11 and 618 of SEQ ID NO: 1 has been identified, it may be useful to confirm the result. In one embodiment, a functional assay may be used to confirm that the nematode is macrocyclic lactone resistant. For example, the *Dirofilaria immitis* nematode may be exposed to a dose of a macrocyclic lactone, e.g. a LD95 dose of a macrocyclic lactone, i.e. a dose of the compound that is lethal to 95% of *Dirofilaria immitis*.

Kits and Commercial Packages

In embodiments of the invention, probes of the invention may be provided to a user as a kit. A kit of the invention may contain one or more probes of the invention. For example, a kit may comprise a probe capable of determining the genotype of a nematode at a position in P-glycoprotein of the nematode corresponding to position 11 of SEQ ID NO: 1; or a probe capable of determining the genotype of a nematode at positions in P-glycoprotein of the nematode at positions corresponding to positions 11 and 618 of SEQ ID NO: 1.

The kit may further comprise one or more reagents, buffers, packaging materials, instructions for using the kit and containers for holding the components of the kit.

Uses of the Methods and Kits

Methods of the invention and kits to carry out the methods may have research, medical and industrial applications. The invention finds broad application in the management of heartworms in infected animals and in detecting macrocyclic lactone resistant *Dirofilaria immitis* nematodes in an area. Representative, non-limiting applications of the invention may include the detection, quantification and/or diagnosis of the existence of individuals or populations of *Dirofilaria immitis* that are not susceptible to normal doses of macrocyclic lactone for prophylaxis or therapy. In one embodiment, the ability to detect and quantify nucleic acid molecules of the invention is valuable insofar as it will instruct a practicing veterinarian to prescribe, and/or alter, a chemotherapeutic regimen for an animal infected with *Dirofilaria immitis* nematodes bearing the GG genotype in P-glycoprotein at a position corresponding to position 11 of SEQ ID NO: 1, or to *Dirofilaria immitis* nematodes bearing the GG genotype in P-glycoprotein at positions corresponding to positions 11 and 618 of SEQ ID NO: 1. Identification of such macrocyclic lactone resistant *Dirofilaria immitis* nematodes may instruct a veterinarian to prescribe, and/or switch from macrocyclic lactone therapy alone to, a therapy that may include alternative agents, such as an adulticide (e.g. arsenic based drugs), diethylcarbamazine, antibiotics such as tetracycline, and combinations of one or more thereof in order to achieve cure and/or to minimize the spread of the resistant strain. Alternatively, a veterinarian may prescribe an atypical dosage (e.g. a higher than normal dosage), or adjust the current dosage, of a macrocyclic lactone and/or treatment regimen using a macrocyclic lactone in the treatment of an animal infected with a macrocyclic lactone resistant nematode. Typical recommended dose rates for macrocyclic lactone preventatives include, for example, 6 µg/kg for ivermectin; 500 mg/kg for milbemycin oxime; 3 µg/kg (monthly) moxidectin; and 6 mg/kg for selamectin. A veterinarian may also combine one or more of the treatment approaches and therapies noted above in any combination suitable to treat an animal infected with a *Dirofilaria* spp. nematode, e.g. a macrocyclic lactone resistant *Dirofilaria immitis* nematode. For example, a veterinarian may treat such an animal with an adulticide, such as an arsenic based drug, and then follow up with a microfilaricide, such as a macrocyclic lactone or diethylcarbamazine.

In one instance, an arsenic based drug may used to treat an animal infected with a macrocyclic lactone resistant *Dirofilaria immitis* nematode. An arsenic based drug may include, but is not limited to, melarsomine dihydrochloride. Melarsomine dihydrochloride may be used, for example, at a dose of 2.5 mg/kg, twice, 24 hours apart. This may be repeated in 4 months depending on the response to the first treatment and the condition, age, and use of the animal. However, a skilled person would understand that the dosage may vary depending on the severity of the infection. For example, an infected animal such as a dog with severe (class 3) disease may receive one dose and allowed to recover for a few months before receiving the complete set of 2 doses.

In another instance, diethylcarbamazine may used to treat an animal infected with a macrocyclic lactone resistant *Dirofilaria immitis* nematode. Diethylcarbamazine may be used, for example, at a dose of 25 to 50 mg per pound of an animal. The duration of administration may depend on the condition being treated, response to the medication and the development of any adverse effects.

In another instance, an antibiotic may used to treat an animal infected with a macrocyclic lactone resistant *Dirofilaria immitis* nematode. Said antibiotic may include, but is not limited to, tetracycline. A tetracycline, such as doxycycline, which targets the Wolbachia endosymbionts in *Dirofilaria immitis* may be used, for example, at a dose of 10 mg/kg/day for 40 days.

In a further instance, another antihelminthic agent may be used. Such other antihelminthic agent may include, but is not limited to, acaciasides. An acaciaside may be used, for example, at a dose of 10 mg/kg/day for 7 days.

In another embodiment, the detection of *Dirofilaria immitis* nematodes populations with the above mentioned genotype in P-glycoprotein may instruct a veterinarian to prescribe the use of alternative agents, such as diethylcarbamazine as a prophylactic to protect susceptible animals, e.g. dogs.

In one instance, diethylcarbamazine may be used to prevent an animal from becoming infected with a macrocyclic lactone resistant *Dirofilaria immitis* nematode. In this regard, diethylcarbamazine may be used, for example, at a dose of 3 mg per pound of an animal once daily.

In another embodiment, a kit of the invention may be useful in as a commercial product in the detection of macrocyclic lactone resistant *Dirofilaria immitis* nematodes. Such a product may be suitable for use by, without limitation, a veterinarian, a physician, a pet owner, a farmer, a zoo keeper, an epidemiologist, or another consumer in need thereof.

The invention is further illustrated by the following, non-limiting examples.

EXAMPLES

Example: 1

Material and Methods

Samples

Four groups of samples were available. Group A corresponds to thirty nine naïve individual worms that were never been exposed to macrocyclic lactones. Group B corresponds to thirty five individual worms that were exposed, or their ancestors were likely exposed to macrocyclic lactone in Florida, Louisiana and Texas. For these samples, the treatment history of the dogs is not precise however macrocyclic lactones are commonly used in these regions. Group C corresponds to one hundred seventeen individual microfilaria that showed in an in vitro assay low sensitivity to IVM. Group D corresponds to thirty three individual worms that were exposed, or their ancestors were likely exposed to macrocyclic lactones in Japan. For these samples, the treatment history of the dogs is not precise however macrocyclic lactones are commonly used in Japan.

Experiment

Microfilariae were collected from three dogs named Tip, Kendall and Tootie. These microfilaria are from the same population of Group C. In vitro assay on these microfilariae from each individual dog was performed using one dose of IVM lethal dose 95% (IVM-LD$^{95}$) which means that at that dose 95% of the naïve microfilaria should died. The microfilaria that died was counted. Then, the microfilaria was incubated in a second dose of IVM that correspond to two times the IVM-LD$^{95}$. The microfilariae that died were counted.

Molecular Biology

The genomic DNA for the individual adult worms was extracted with DNeasy™ kit from Qiagen (Qiagen Inc, Mississauga, Canada). The genomic DNA extraction of individual microfilaria was extracted using QIAamp DNA kit from Qiagen followed by Repli-g® screening kit from Qiagen which allow amplifying the full genome from a very small amount of DNA. Only few sequences of *D. immitis* are available in GenBank so bioinformatic research was performed based on *O. volvulus, B. malayi, C. elegans* or *H. contortus* sequences, to be able to amplify a segment of 620 bp of the *D. immitis* P-glycoprotein gene. The amplification was done by PCR using the following primers: Pgp-1-sens 5' gga caa tta tcc ggt ggt ca 3' [SEQ ID NO: 2] and Pgp-1-antisens 5' tcg caa att tcc ttc cac tt 3' [SEQ ID NO: 3]. Denaturation was performed at 94° C. for 45 s; annealing at 56° C. for 45 s; and extension at 68° C. for 2 min for 35 cycles. PCR amplification was confirmed by gel electrophoresis at 100V for 40 min with a 1% agarose gel containing 0.5 µg/ml ethidium bromide. PCR products were sequenced using the 3730XL DNA Analyser system (McGill University/Genome Quebec Innovation Centre). High Fidelity Platinium® Taq DNA polymerase (Invitrogen) was used in the PCR reaction to avoid the introduction of errors during amplification. Each individual chromatogram was analysed with Sequencher™ 4.7 software (Gene Codes Corporation, Ann Arbor, Mich. 48108, USA). This program allowed the discrimination at each nucleotide and selection for only secondary peaks which were more than 90% of the major nucleotide peak on the chromatogram. This high level of discrimination provided confidence in determining homozygosity and heterozygosity at the polymorphic positions.

Statistical Analysis

Genotypic frequencies of the single nucleotide polymorphism (SNP) of Group C (macrocyclic lactone low responders) were compared to the genotypic frequencies of the SNPs of the three other groups using $x^2$ test and Fisher's exact test.

The linear regression to assess if there is a correlation between the genotype of P-glycoprotein of the microfilaria from Group C and their corresponding Ivermectin-$LD.^{95}\%$ phenotype was performed using GraphPad Prism version 5.00 for Windows, GraphPad Software, San Diego Calif. USA.

Results

Two common SNPs were found in the fragment analysed [FIG. 1; SEQ ID NO: 1]. One was located at position 11 (A11G) of that fragment analysed while the second one was at position 618 (A618G). The A11G SNP was in a coding region just before the second ATP binding domain and resulted in an amino change from a lysine to an arginine. The A618G SNP was located in a non coding region. Based on sequences available from *O. volvulus*, *B. malayi* and *C. elegans*, the fragment analysed would start approximately at position 1200 of the amino acid sequence.

Among the 37 adult worms that were genotyped in Group A, the genotype frequencies at position 11 of homozygotes AA, GG and heterogygotes AG were 81.1%, 0% and 18.9% respectively. Among the 34 adult worms that were genotyped in Group B, the genotype frequencies at position 11 of homozygotes AA, GG and heterogygotes AG were 91.2%, 2.9% and 5.9% respectively. Among the 92 microfilariae that were genotyped in Group C, the genotype frequencies at position 11 of homozygotes AA, GG and heterogygotes AG were 57.6%, 35.9% and 6.5% respectively. Among the 33 adult worms that were genotyped in Group D, the genotype frequencies at position 11 of homozygotes AA, GG and heterogygotes AG were 100%, 0% and 0% respectively [FIG. 2]. The homozygote AA genotype frequency was significantly lower in Group C compared to Group A (p=0.008), Group B (p=0.0001) and Group D (p=0.000006). The homozygote GG genotype frequency was significantly higher in Group C compared to Group A (p=0.000001), Group B (p=0.00005) and Group D (p=0.000006) [Table 1]. Moreover, allele A and allele G frequency were significantly lower and higher respectively in Group C compared to Group A (p=0.000002), Group B (p=0.0000001) and Group D (p=0.00000000001) [not shown].

TABLE 1

Comparison of genotype frequency of SNP at position 11 of Group C versus the other three groups

| | GroupC | | |
|---|---|---|---|
| | AA p-value | AG p-value | GG p-value |
| GroupA | 0.008 | 0.04 | 0.000001 |
| GroupB | 0.0001 | 0.6 | 0.00005 |
| GroupD | 0.000006 | 0.1 | 0.000006 |

Figure 3:
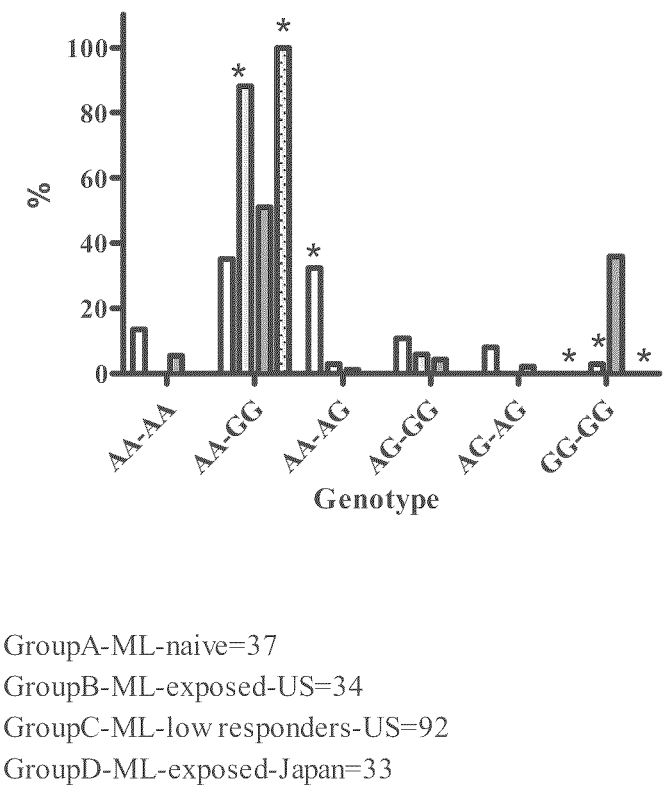
FIG. 3: Genotype frequency of the combined SNP at positions 11 and 618 of P-glycoprotein gene (*=p-value significant).

The genotype from SNP at position 11 and 618 was combined [FIG. 3]. For example, AA-GG genotype corresponded to genotype AA at position 11 and genotype GG at position 618. Among the 9 possible combined genotypes, only six different genotypes were found in the total sample population, AA-AA, AA-GG, AA-AG, AG-GG, AG-AG and GG-GG. In Group D, only genotype AA-GG was found. Some genotypes were not found in some groups like GG-GG in Group A, AG-AG and AA-AA in Group B. Group C was the only group where all six different genotype were found. Interestingly, the genotype GG-GG was significantly higher in Group C compared to Group A (p=0.000001), Group B (p=0.00005) and Group D (p=0.000006) [Table 2] and was not found in Group A and D.

TABLE 2

Comparison of genotype frequency of combined SNP at position 11 and 618 of Group C versus the other three groups

| | GroupC | | | | | |
|---|---|---|---|---|---|---|
| | AA-AA p-value | AA-GG p-value | AA-AG p-value | AG-GG p-value | AG-AG p-value | GG-GG p-value |
| Group A | 0.1 | 0.07 | 0.0000007 | 0.1 | 0.1 | 0.000001 |
| Group B | 0.2 | 0.00007 | 0.4 | 0.5 | 0.5 | 0.00005 |
| Group D | 0.2 | 0.00000002 | 0.7 | 0.3 | 0.5 | 0.000006 |

Figure 4:
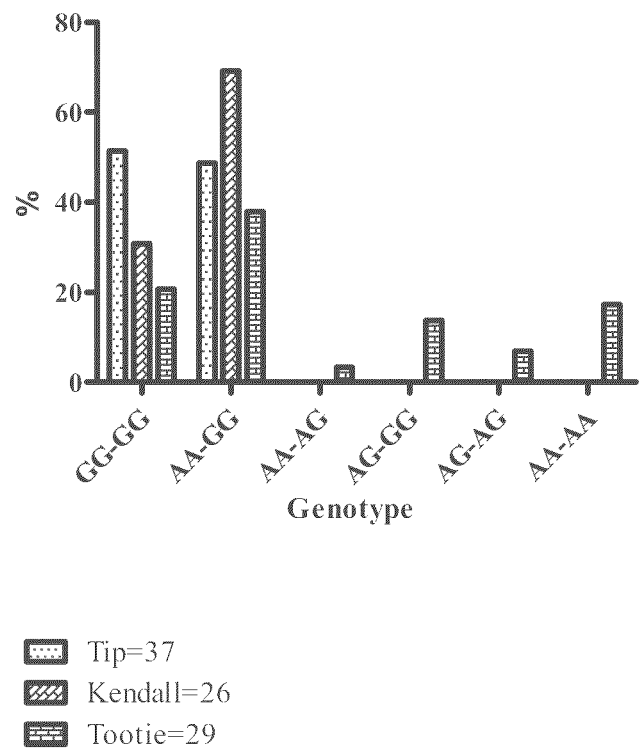
FIG. 4: Genotype frequency of the combined SNP at positions 11 and 618 of P-glycoprotein of Group C.

Group C is a group of individual microfilaria isolated from three dogs: Tip, Kendall and Tootie. Microfilaria from Tip and Kendall were only of genotypes GG-GG and AA-GG, whereas the six different genotypes were all found in microfilaria from Tootie [FIG. 4]. The frequency of GG-GG genotype was 51.3%, 30.7% and 20.7% in microfilaria collected from Tip, Kendall and Tootie respectively.

The in vitro study [Table 3] showed that only 8% and 39% of the microfilaria from Tip died after exposure to one dose of IVM at the $LD_{95}\%$ which is the dose where 95% of the microfilaria should died. By exposing the microfilaria from Tip at the double $LD_{95}\%$, only 24.1% and 50.4% died. 56% and 79% of the microfilaria from Kendall and Tootie died after one dose of IVM at the $LD_{95}\%$, however 99.2% and 100% of the microfilaria from that two dogs died after exposure the double $LD_{95}\%$.

TABLE 3

Results of in vitro assay

| IVM | Tip | Tip | Kendall | Tootie |
|---|---|---|---|---|
| $LD_{95}$ | 5/62.2 8% | 13/33.3 39% | 14.2/25.6 56% | 27.5/35 79% |
| $LD_{95}$ (x2) | 14.2/58.8 24.1% | 16.3/32.3 50.4% | 25/25.2 99.2% | 44.2/44.2 100% |

Figure 5:
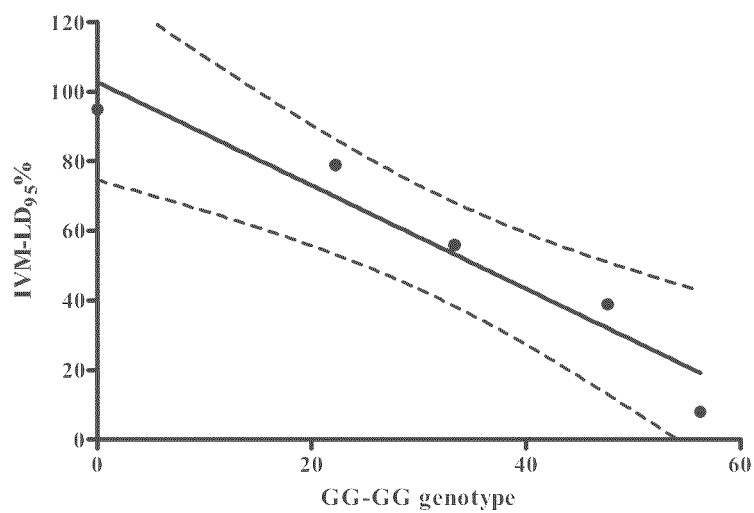
FIG. 5: Linear regression of P-glycoprotein genotype GG-GG versus IVM-$LD_{95}$%.

A significant correlation (Goodness of fit $r^2=0.93$; $p=0.008$) [FIG. 5] was found between the GG-GG genotype of the microfilaria from Tip, Kendall and Tootie and their IVM-$LD_{95}$% phenotype.

Discussion

From different reports on veterinary nematode, and more recently on *O. volvulus*, which is phylogenetically more closely related to *D. immitis*, it is known now that genetic selection occurs under repeated macrocyclic lactone treatment in ABC transporter genes. With the new emergence of dogs with low responses to macrocyclic lactone, it is important to have reliable genetic marker to detect genetic changes associated with a potential spread of macrocyclic lactone resistance.

The study is unique because *D. immitis* samples with different treatment history and from different regions were compared. In this regards, worms that never been exposed to IVM were compared to samples that were exposed to macrocyclic lactone and to samples that showed low response to IVM after strong exposure to the drug. Each individual sample was sequenced for a specific region of P-glycoprotein gene which was not available in GenBank.

The data shows that there is a clear selection pressure of macrocyclic lactone on P-glycoprotein gene in *D. immitis*. The GG-GG genotype of P-glycoprotein may be used as a genetic marker tool in the field to follow the spread of IVM/macrocyclic lactone sub-optimal responders in dogs infected with heartworms.

Example: 2

As noted in Example 1, a strong correlation was found between a GG-GG genotype in a P-glycoprotein (accession number: HM596853—SEQ ID NO: 6) and an IVM insensitivity phenotype in *D. immitis* mf in an in vitro assay; the more insensitive the mf were to IVM, the higher the frequency of the GG-GG genotype. In this example, the response to treatment in a heartworm-positive dog, originally from New Orleans, is reported and the frequency of the Pgp gentotype associated with lack of macrocyclic lactone sensitivity was determined.

Materials and Methods

Case:

The dog was a male neutered Labrador mix, born in February, 2006, that weighed approximately 31 kg. He was a rescue dog from New Orleans, La., U.S.A., collected by the Boudreaux Rescue Crew, New Orleans, and subsequently transferred to Canada where he was adopted in January, 2008.

Diagnosis:

The dog was brought to the Main West Animal Hospital (MWAH) in Welland, Ontario on Jun. 6, 2008 (day 1) for a check up. Blood collected from the dog tested positive with a heartworm antigen test (PetChek® PF (IDEXX Laboratories, Westbrook, Me.)) and contained mf of *D. immitis*. On Jun. 11, 2008 (day 6), initial work-up (bloodwork, thoracic radiographs, physical exam, urinalysis) was performed. Auscultation revealed a mild increase in bronchovesicular sounds in the lungs and a grade III-IV/VI heart murmur. The remainder of the physical exam was unremarkable. Thoracic radiography revealed moderate right-sided heart enlargment and an interstitial lung pattern in the caudodorsal lung field. These examinations indicated a diagnosis of class 2 heartworm disease.

Treatment History:

Adulticide treatment was initiated on Jun. 11, 2008 (day 6) with 2.5 mg/kg IM melarsomine dihydrochloride (Immiticide®, Merial Inc.). The treatment was followed by two IM treatments with 2.5 mg/kg melarsomine dihydrochloride on July 9 and July 10 (days 34, 35). Over the following 90 days, in order to eliminate circulating mf, the dog was treated on one occasion with milbemycin oxime (MO) and on two occasions with IVM (see Table 4). On days 159 and 160, four months after the last dose of adulticide, the dog was again treated with 2.5 mg/kg melarsomine dihydrochloride IM. The subsequent diagnostic testing and microfilaricidal treatments are summarized in Table 4.

Heartworm Antigen Tests:

During the treatment of the dog, several heartworm antigen tests were conducted, including DiroChek® (Synbiotics Corporation, San Diego, Calif.) and PetChek® PF (IDEXX Laboratories, Westbrook, Me.), which are microwell ELISA tests, and SNAP® PF (IDEXX Laboratories, Westbrook, Me.), a membrane format test designed for rapid in-clinic use (see Table 4).

Knott's Test:

Nine ml of 2% formalin and 1 ml blood (collected in EDTA) were mixed in a centrifuge tube. Centrifugation was performed in a LW Scientific EZ Swing SK centrifuge at 3000 rpm (604 $m/s^2$) for 5 min. The supernatant fluid was discarded. A drop of 0.1% methylene blue solution was added to the pellet at the bottom of the centrifuge tube, mixed, and a drop of stained mixture examined under the microscope for *D. immitis* mf. Table 4 indicates when this test was carried out and, when determined, the level of microfilaremia.

Genetic Analysis:

On May 12, 2010 (day 706), a blood sample (5 ml) was collected in EDTA for genetic investigation of mf. The blood was highly microfilaremic. Fifty-three live, individual mf were isolated from the blood sample. Genomic DNA from individual mf was extracted using a QIAamp DNA kit (Qiagen Inc, Mississauga, Canada), followed by amplification of the full genome with a Repli-g® screening kit (Qiagen Inc, Mississauga, ON, Canada). PCR amplification of the P-glycoprotein (Pgp) gene was performed using primers Pgp-1-sense (5' gga caa tta tcc ggt ggt ca 3') [SEQ ID NO: 2] and Pgp-1-antisense (5' tcg caa att tcc ttc cac tt 3') [SEQ ID NO: 3]. As described herein, a genotype of GG at positions in P-glycoprotein corresponding to positions 11 and 618 in SEQ ID NO:1 was found to correlate with insensitivity to MLs. Denaturation was performed at 94° C. for 45 s, annealing at 56° C. for 45 s and extension at 68° C. for 2 min for 35 cycles. High Fidelity Platinum® Taq DNA polymerase (Invitrogen, Burlington, ON, Canada) was used in the PCR to minimize the introduction of errors during amplification. PCR amplification was confirmed by electrophoresis through a 1% agarose gel. PCR products were sequenced using the 3730XL DNA Analyser system (Genome Quebec Innovation Centre, McGill University). Each chromatogram was analyzed with Sequencher™ 4.7 software (Gene Codes Corporation, Ann Arbor, Mich.).

Deviation from Hardy-Weinberg Equilibrium:

The Wright's hierarchical F-statistic was calculated for a total of ten different single nucleotide polymorphisms (SNPs) from three genes. In addition to the two SNPs in P-glycoprotein, measured above, an additional eight SNPs were investigated, two in a β-tubulin gene (accession number: HM596854—SEQ ID NO: 4), and six in a heat shock protein gene (accession number: HM596851—SEQ ID NO: 5), based on a previous analysis performed to determine genetic baseline information for *D. immitis*, which showed polymorphism at these sites.

Statistical Analysis:

Genotype frequencies were compared using Fisher's exact test.

Results

Treatment:

Two days after the last of three doses of melarsomine dihydrochloride in July 2008 (i.e., on day 37), the dog showed transitory signs consistent with death of adult heartworms (elevated rectal temperature, lethargy, cough, increased lung sounds). Beginning on day 41, these signs were managed with prednisone (Apo-Prednisone; Apotex, Toronto, ON, Canada), 1.3 mg/kg bid for 6 days.

Following the administration of milbemycin oxime (MO) per os at 0.74 mg/kg on day 74, IVM per os at 50 ug/kg on day 95, and IVM per os at 200 ug/kg (4× the normal microfilaricidal dose rate) on day 125, the dog remained continually microfilaremic. On day 207, six weeks after the second treatment regimen of melarsomine dihydrochloride, on days 159 and 160, a Knott's test was still positive, so the dog was again treated with 200 μg/kg IVM per os. One month later, on day 242, a *D. immitis* antigen test was negative, which confirmed that the dog was free of adult worms. However, the dog was still microfilaremic. Thus, beginning on day 243, the dog was given MO per os at 0.74 mg/kg every 2 weeks on four occasions (see Table 4). Despite this, the dog remained microfilaremic on day 298. It was therefore administered MO per os at 1.1 mg/kg on days 298, 312, 326, 340 and 354. On day 356, blood was collected from the dog and examined: mf were still present, and a *D. immitis* antigen test was still negative. On day 375, a blood sample was sent to Animal Health Laboratory, University of Guelph (AHLUG): microfilaremia was 6530 mf/ml, and an antigen test was still negative (see Table 4). As a result, beginning on day 384, the dog was administered MO per os at 2.0 mg/kg once daily for 7 days. On day 420, the dog had a microfilaraemia of 355 mf/ml. On day 420, the dog was again treated with MO per os at 2.0 mg/kg, and this was continued once daily for 8 days. Despite this second high-dose regimen, on day 480, while still testing negative with a heartworm antigen test, the dog had a microfilaremia of 1810 mf/ml.

Genetic Analysis:

Blood was collected from the dog on day 706 and microfilariae in the blood isolated for genetic analysis. Between day 428 and day 706, the dog was not treated with macrocyclic lactones. The frequency of the GG-GG genotype in the Pgp gene was 45.3% in the live mf isolated from the blood sample. The GG-GG genotype refers to the genotype of Pgp at positions corresponding to positions 11 and 618 of SEQ ID NO:1]

Figure 6:
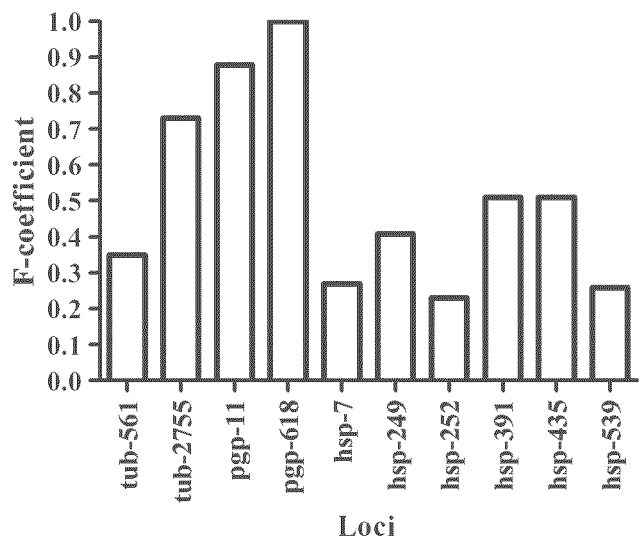
FIG. 6: F-coefficient, or deviation from Hardy-Weinberg equilibrium, for ten SNPs in three genes: β-tubulin (tub), heat shock protein 60 (hsp), P-glycoprotein (pgp). F=+1, 100% homozygous; F=−1, 100% heterozygous. The number next to the gene corresponds to the position of the SNP in the segment analyzed.

Deviation from Hardy-Weinberg Equilibrium:

The F coefficient varied from 0.23 to 1 for the different SNPs, indicating an excess of homozygosity in this population (FIG. 6). In particular, the excess of homozygosity was very high for the Pgp SNPs (F coefficients of 0.88 and 1).

TABLE 4

Diagnostic testing and treatment history for dog between 2008 and 2009.

| Date (day) | Antigen test Name-result (+ve or −ve) | Adulticide (melarsomine) * dosage | Microfilariae concentration in blood (mf/ml) | Microfilaricide drug dosage (PO) | Comments |
|---|---|---|---|---|---|
| 2008 | | | | | |
| June 6 (1) | PetChek +ve[a] | | Knott's test +ve[a] | | |
| June 11 (6) | | 2.5 mg/kg | | | Classified as Class 2 heartworm disease |
| July 9 (34) | | 2.5 mg/kg | | | |
| July 10 (35) | | 2.5 mg/kg | | | |
| August 18 (74) | | | | MO, 0.74 mg/kg | |
| September 3 (90) | | | Knott's test +ve[a] | | |
| September 8 (95) | | | | IVM, 50 μg/kg | |
| October 6 (123) | | | Knott's test +ve[a] | | |
| October 8 (125) | | | | IVM, 200 μg/kg | |
| November 10 (158) | | | Knott's test +ve[a] | | |
| November 11 (159) | | 2.5 mg/kg | | | |
| November 12 (160) | | 2.5 mg/kg | | | |
| December 12 (190) | | | | MO, 0.74 mg/kg | |
| December 29 (207) | | | Knott's test +ve[a] | | |
| December 30 (208) | | | | IVM, 200 μg/kg | |
| 2009 | | | | | |
| February 2 (242) | SNAP −ve[a] | | Knott's test +ve[a] ≥100[b] | | Interpretation: no adult heartworms |
| February 3 (243) | | | | MO, 0.74 mg/kg | |
| February 17 (257) | | | | MO, 0.74 mg/kg | |
| March 3 (271) | | | Knott's test +ve[a] ≥100[b] | MO, 0.74 mg/kg | |
| March 17 (285) | | | | MO, 0.74 mg/kg | |
| March 30 (298) | | | Knott's test +ve[a] ≥100[b] | MO, 1.1 mg/kg | |
| April 13 (312) | | | | MO, 1.1 mg/kg | |
| April 27 (326) | | | | MO, 1.1 mg/kg | |
| April 28 (327) | | | Knott's test +ve[a] | | |
| May 11 (340) | | | | MO, 1.1 mg/kg | |
| May 25 (354) | | | | MO, 1.1 mg/kg | |
| May 27 (356) | SNAP −ve[a] | | Knott's test +ve[a] | | No adult heartworm |

TABLE 4-continued

Diagnostic testing and treatment history for dog between 2008 and 2009.

| Date (day) | Antigen test Name-result (+ve or −ve) | Adulticide (melarsomine) * dosage | Microfilariae concentration in blood (mf/ml) | Microfilaricide drug dosage (PO) | Comments |
|---|---|---|---|---|---|
| June 8 (368) | | | | MO, 1.1 mg/kg | |
| June 15 (375) | DiroChek −ve[c] | | Knott's test +ve[c] 6530 | | No adult heartworm |
| June 24 (384) | | | | MO, 2.0 mg/kg daily for 7 days | |
| July 30 (420) | | | Knott's test +ve[c] 355 | MO, 2.0 mg/kg daily for 8 days | |
| September 28 (480) | PetChek −ve[a] | | Knott's test +ve[c] 1810 | | |
| 2010 | | | | | |
| May 12 (706) | | | | | Microfilariae collected for genetic analysis |

MO = milbemycin oxime (Interceptor ®); IVM = ivermectin (Ivomec ® Injection for cattle, sheep and swine, Merial Inc.);
* Adulticide = Immiticide ®;
[a]= Main West Animal Hospital (i.e. test carried out in house);
[b]= Idexx Laboratories;
[c]= Animal Health Laboratory, University of Guelph Discussion It was found that mf or adult *D. immitis* from dogs known to be sensitive to MLs had frequencies of the GG-GG genotype in the Pgp gene ranging from 0 to 18.5%, whereas the most IVM-resistant mf (by in vitro assay) had a GG-GG frequency of 51.3%, and the frequency of this genotype was very highly correlated with the level of insensitivity to IVM. In mf from the case described here, the GG-GG genotype frequency was 45.3% (p=0.002 compared with mf from a susceptible canine infection, and p=0.000006 compared with adult worms from different susceptible infections, as reported in Example 1). The correlation found in Example 1 between the Pgp genotype and IVM response phenotype appears to reflect the in vivo sensitivity, and suggests a high level of insensitivity to IVM in mf from the described case. The high excess of homozygosity of the Pgp SNPs is consistent with the selection of a particular Pgp genotype as a result of drug pressure. MO and IVM have previously been shown to kill mf at 500 µg/kg and 50 µg/kg, respectively. However, none of the drug regimens used in this case, either at increased dose rates or using multiple treatment protocols (e.g., MO at 2.0 mg/kg daily for 8 days) cleared the mf. Given the treatment response phenotype and the genotype which has been shown to correlate with ML insensitivity, a conclusion of ML resistance in the *D. immitis* in this dog can be made.

Two treatment scenarios, administration of ML preventives to dogs containing developing stages of *D. immitis* which are older than 3.5 months of age, and administration of heartworm preventives to microfilaremic dogs, have been suggested to potentially lead to development of ML resistance in *D. immitis*. Resistance is more likely to develop in areas of more intense transmission and hence higher drug pressure. Prophylaxis unquestionably remains the best tool to control heartworm infection, provided the drugs are effective. Having said that, given anecdotal reports of lack of response to ML heartworm preventives, there is reason to believe that the case described here is probably not the only dog infected with ML-resistant *D. immitis*. A survey of the prevalence of ML resistance is therefore urgently needed. In this regard, the genotype assay described here, and in Bourguinat et al. may be useful. New strategies may need to be developed for controlling ML-resistant *D. immitis*. A survey should indicate whether this genotype is confined to a specific focus or is more widespread; such knowledge could be important for guiding the development and use of possible alternative control strategies.

REFERENCES

Ali M M, Mukhtar M M, Baraka O Z, Homeida M M, Kheir M M & Mackenzie C D (2002). Immunocompetence may be important in the effectiveness of Mectizan (ivermectin) in the treatment of human onchocerciasis. Acta Trop. 84: 49-53.

Ardelli B F & Prichard R K (2004). Identification of variant ABC transporter genes among *Onchocerca volvulus* collected from treated and untreated patients in Ghana, West Africa. Annals Trop. Med. Parasitol. 98: 371-384.

Ardelli B F, Guerriero S B & Prichard R K (2005). Genomic organization and effects of ivermectin selection on *Onchocerca volvulus* P-glycoprotein. Mol. Biochem. Parasitol. 143: 58-66.

Ardelli B F, Guerriero S B & Prichard R K (2006a). Ivermectin imposes selection pressure on P-glycoprotein from *Onchocerca volvulus*: linkage disequilibrium and genotype diversity. Parasitology 132: 375-386.

Ardelli B F, Guerriero S B & Prichard R K (2006b). Characterization of a half-size ATP-binding cassette transporter gene which may be a useful marker for ivermectin selection in *Onchocerca volvulus*. Mol. Biochem. Parasitol. 145: 94-100.

Ardelli B F & Prichard R K (2007). Reduced genetic variation of an *Onchocerca volvulus* ABC transporter gene following treatment with ivermectin. Trans. Roy. Soc. Trop. Med. Hyg. 101: 1223-1232.

Atkins C. Canine Heartworm Disease: Current Treatment and Prevention Approaches. The 26.sup.th annual WALTHAM® Diets/OSU Symposiun. Small Animal Cardiology 2002.

Awadzi K, Boakye D A, Edwards G, Opoku N O, Attah S K, Osei-Atweneboana M Y, Lazdins-Helds J K, Ardrey A E, Addy E T, Quartey B T, Ahmed K, Boatin B A, Soumbey-Alley E W (2004a). An investigation of persistent microfilaridermias despite multiple treatments with ivermectin, in two onchocerciasis-endemic foci in Ghana. Ann. Trop. Med. Parasitol. 98: 231-49.

Awadzi K, Attah S K, Addy E T, Opoku N O, Quartey B T, Lazdins-Helds J K, Ahmed K, Boatin B A, Boakye D A, Edwards G (2004b). Thirty-month follow-up of sub-optimal responders to multiple treatments with ivermectin, in two onchocerciasis-endemic foci in Ghana. Ann. Trop. Med. Parasitol. 98: 359-70.

Bennett J L, Williams J F & Dave V, 1988. Pharmacology of ivermectin. Parasitol. Today 4: 226-228.

Blackhall W J, Pouliot J-F, Prichard R K & Beech R N (1998a). *Haemonchus contortus*: Selection at a glutamate-gated chloride channel gene in ivermectin- and moxidectin-selected strains. Exp. Parasitol. 90: 42-48.

Blackhall W, Liu H Y, Xu M, Prichard R K & Beech R N (1998b). Selection at a P-glycoprotein gene in ivermectin- and moxidectin-selected strains of *Haemonchus contortus*. Mol. Biochem. Parasitol. 95: 193-201.

Blackhall W J, Prichard R K & Beech R N (2003). Selection at a γ-aminobutyric acid receptor gene in *Haemonchus contortus* resistant to avermectins/milbemycins. Mol. Biochem. Parasitol. 131: 137-145.

Boersema J H. Eysker M. & Nas J W. 2002. Apparent resistance of Parascaris equorum to macrocyclic lactones. Vet. Rec. 150: 279-281.

Bourguinat, C., Pion, S. D. S., Kamgno, J., Gardon, J., Duke, B. O. L., Boussinesq, M. & Prichard, R. K. (2007). Genetic selection of low fertile *Onchocerca volvulus* by ivermectin treatment. PLoS Neg. Trop. Dis. 1(1)e72: 12-22.

Bourguinat, C., Ardelli, B. F., Pion, S. D. S., Kamgno, J., Gardon, J., Duke, B. O. L., Boussinesq, M., & Prichard, R. K. (2008). P-glycoprotein-like protein, a possible genetic marker for ivermectin resistance selection in *Onchocerca volvulus*. Molecular & Biochemical Parasitology, 158: 101-111.

Bourguinat C, Keller K, Blagburn B, et al. Correlation between loss of efficacy of macrocyclic lactone heartworm preventatives and P-glycoprotein genotype. Vet Parasitol 2011 American Heartworm Society (in press) doi:10.1016/j.vetpar.2011.01.024.

Bourguinat C, Keller K, Prichard R K, et al. Genetic polymorphism in *Dirofilaria immitis*. Vet Parasitol 2011 American Heartworm Society (in press). doi:10.1016/j.vetpar.2011.01.023.

Bowman D D, et al., 1992. Effects of long-term administration of ivermectin and milbemycin oxime on circulating microfilariae and parasite antigenemia in dogs with patent heartworm infections. In: Soll M D (Ed.) Proceedings of the Heartworm Symposium '92. Amer. Heartworm Soc., Batavia, Ill., pp. 151-158.

Bowman D D, Neumann N R, Rawlings C, et al. Effects of avermectins on microfilariae in dogs with existing and developing heartworm infections. In: R. L. Seward, eds. Recent Advances in Heartworm Disease: Symposium '01. American Heartworm Society, Batavia, Ill. 2001; 173-178.

Bowman D D, Torre C J. The effects of preventative dosages of macrolide treatments on circulating microfilariae in dogs with patent heartworm—*Dirofilaria immitis*—infections. US Companion Animal Health 2006; 9-11.

Churcher T S, Schwab A E, Prichard R K, et al. An analysis of genetic diversity and inbreeding in *Wuchereria bancrofti*: implications for the spread and detection of drug resistance. PLoS Neg Trop Dis 2008; 2: e211(1-9).

Courtney C H, Zeng Q T & Maler M M, 1998. The effect of chronic administration of milbemycin oxime and ivermectin on microfilaremias in heartworm-infected dogs. In: Seward R L (Ed.) Recent Advances in Heartworm Disease: Symposium '98. Amer. Heartworm Soc., Batavia, Ill., pp. 193-199.

Dent J A, Smith M M, Vassilatis D K & Avery L, (2000). The genetics of ivermectin resistance in *Caenorhabditis elegans*. Proc. Nat. Acad. Sci., USA 97: 2674-2679.

Eng J K L & Prichard R K (2005). A comparison of genetic polymorphism in populations of *Onchocerca volvulus* from untreated- and ivermectin-treated patients. Mol. Biochem. Parasitol. 142: 193-202.

Eng J K L, Blackhall W J, Osei-Atweneboana M Y, Bourguinat C, Galazzo D, Beech R N, Unnasch T R, Awadzi K, Lubega G W & Prichard R K (2006). Ivermectin selection on β-tubulin: Evidence in *Onchocerca volvulus* and *Haemonchus contortus*. Mol. Biochem. Parasitol. 150: 229-235.

Feng X-P, Hayashi J, Beech R N & Prichard R K 2002. Study of the nematode putative GABA type A receptor subunits: Evidence for modulation by ivermectin. J. Neurochem. 83:870-878.

Geary T G (2005). Ivermectin 20 years on: maturation of a wonder drug. Trends Parasitol. 21: 530-532.

Hampshire V A (2005). Evaluation of efficacy of heartworm preventive products at the FDA. Vet. Parasitol. 133: 191-195.

Hearn F P & Peregrine A S (2003). Identification of foals infected with Parascaris equorum apparently resistant to ivermectin. JAVMA 223: 482-5, 455.

Kaplan R M (2004b). Drug resistance in nematodes of veterinary importance: a status report. Trends Parasitol. 20: 477-481.

Le Jambre L F, Lenane I J & Wardrop A J (1999). A hybridisation technique to identify anthelmintic resistance genes in *Haemonchus*. Int. J. Parasitol. 29: 1979-1985.

Lespine A, Dupuy J, Alvinerie M, Comera C, Nagy T, Krajcsi P, Orlowski S. Interaction of macrocyclic lactones with the multidrug transporters: the bases of the pharmacokinetics of lipid-like drugs. Curr Drug Metab. 2009 March; 10(3): 272-88.

McManus E C, Pulliam J D. Histopathologic features of canine heartworm microfilarial infection after treatment with ivermectin. Am J Vet Res 1984; 45:91-97.

McCall J W, Ryan W G, Roberts R E & Dzimianski M T, 1998. Heartworm adulticidal activity of prophylactic doses of ivermectin (6 µg/kg) plus pyrantel administered monthly to dogs. In: Seward R L (Ed.) Recent Advances in Heartworm Disease: Symposium '98. Amer. Heartworm Soc., Batavia, Ill., pp. 209-215.

McCall J W, 2005. The safety-net story about macrocyclic lactone heartworm preventives: A review, an update, and recommendations. Vet. Parasitol. 133: 197-206.

Mottier, M. L. & Prichard, R. K. (2008). Genetic analysis of a relationship between macrocyclic lactone and benzimidazole anthelmintic selection on *Haemonchus contortus*. Pharmacogenetics & Genomics, 18: 129-140.

Njue A I, Hayashi J, Kinne L, Feng X-P & Prichard R K (2004). Mutations in the extracellular domains of glutamate-gated chloride channel α3 and β subunits from ivermectin-resistant *Cooperia oncophora* affect agonist sensitivity. J. Neurochem. 89: 1137-1147.

Osei-Atweneboana, M. Y., Eng, J. K. L., Boakye, D. A., Gyapong, J. O. & Prichard, R. K. (2007) Prevalence and intensity of *Onchocerca volvulus* infection and efficacy of ivermectin in endemic communities in Ghana: a two phase epidemiological study. *Lancet* 369: 2021-2029.

Sangster N C, Bannan S C, Weiss A S, Nulf S C, Klein R D & Geary T G (1999). *Haemonchus contortus*: sequence heterogeneity of internucleotide binding domains from P-glycoproteins. Exp. Parasitol. 91: 250-257.

Strote G, Bonow I, & Attah S (1996). The ultrastructure of the anterior end of male *Onchocerca volvulus*: papillae, amphids, nerve ring and first indication of an excretory system in the adult filarial worm. Parasitology 113:71-85.

Trawford, A. F., Burden, F & Hodgkinson, J. (2005). Suspected moxidectin resistance in cyathostomes in two donkey herds at the Donkey Sanctuary, UK. Abstracts of the 20th International Conference of the World Association for the Advancement of Veterinary Parasitology, Christchurch, New Zealand. p 196.

Venco L, McCall J W, Guerrero J, et al. Efficacy of long-term monthly administration of ivermectin on the progress of naturally acquired heartworm infections in dogs. Vet Parasitol 2004; 124:259-268.

Wolstenholme A J, Fairweather I, Prichard R, von Samson-Himmelstjerna G & Sangster N C (2004). Drug resistance in veterinary helminths. Trends Parasitol. 20: 469-476.

Xu M, Molento M, Blackhall W, Ribeiro P, Beech R & Prichard R (1998). Ivermectin resistance in nematodes may be caused by alteration of P-glycoprotein homolog. Mol. Biochem. Parasitol. 91: 327-335.

Diagnosis, prevention and management of heartworm infection in dogs: Guidelines, canine heartworm disease. American Heartworm Society, revised January 2010. Sheldon B. Rubin; Charles Thomas Nelson; Doug Carithers; Wallace Graham; Lynn F. Buzhardt; Stephen Jones; Julie Levy; Dr. Robert Stannard; Carol Robertson-Plouch; Byron Blagburn; John W. McCall; and Dr. Jorge Guerrero.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A kit for determining the responsiveness of a *Dirofilaria* spp. nematode to a macrocyclic lactone, the kit comprising: a probe capable of determining the genotype of the *Dirofilaria* spp. nematode at a position in a P-glycoprotein gene of the nematode corresponding to position 11 of SEQ ID NO: 1 or a nucleotide sequence at least 80% identical to SEQ ID NO: 1; or a probe capable of determining the genotype of the *Dirofilaria* spp. nematode at positions in a P-glycoprotein gene of the nematode corresponding to positions 11 and 618 of SEQ ID NO: 1; wherein said probe comprises a label and wherein the genotype GG at said position corresponding to position 11 in SEQ ID NO: 1 or the genotype GG at said positions corresponding to positions 11 and 618 in SEQ ID NO: 1, indicates that the nematode is likely to be resistant to said macrocyclic lactone.

2. The kit according to claim 1, wherein said *Dirofilaria* spp. nematode is *Dirofilaria immitis*.

3. The kit according to claim 1, wherein the macrocyclic lactone is selected from the group consisting of ivermectin, selamectin, milbemycin oxime and moxidectin.

4. The kit according to claim 1, wherein the probe is an oligonucleotide, a primer, an aptamer or an antibody.

5. A kit according to claim 1 wherein the label is a radioactive, enzymatic or fluorescent tag.

6. A kit according to claim 1 further comprising one or more reagents, buffers, packaging materials, instructions for using the kit or containers for holding components of the kit.

7. A method for treating an animal infected with a *Dirofilaria* spp. nematode, the method comprising determining for an individual or population of *Dirofilaria* spa nematodes in an area, the genotype of said individual or population of nematodes at a position in a P-glycoprotein gene of said individual or population of nematodes corresponding to position 11 in SEQ ID NO:1 or a nucleotide sequence at least 80% identical to SEQ ID NO:1, or corresponding to positions 11 and 618 in SEQ ID NO:1 or a nucleotide sequence at least 80% identical to SEQ ID NO:1, wherein said determining comprises the use of a probe which binds to a nucleotide sequence corresponding to position 11 in SEQ ID NO:1, or a nucleotide sequence at least 80% identical to SEQ ID NO:1 or which binds to a nucleotide sequence corresponding to positions 11 and 618 of SEQ ID NO:1 or a nucleotide sequence at least 80% identical to SEQ ID NO:1; or which binds to a position in P-glycoprotein corresponding to position 11 of SEQ ID NO:1, or a sequence at least 80% identical to SEQ ID NO:1 or a position in P-glycoprotein corresponding to position 11 and 618 of SEQ ID NO:1, or a nucleotide sequence at least 80% identical to SEQ ID NO:1 and administering to said animal an adjusted dosage of a macrocyclic lactone, or administering an arsenic therapy, diethylcarbamazine, antibiotics, or a combination of one or more thereof, if the individual or population of nematodes has the genotype GG at a position in the P-glycoprotein gene corresponding to position 11 in SEQ ID NO: 1 or a nucleotide sequence at least 80% identical to SEQ ID NO:1; or corresponding to positions 11 and 618 in SEQ ID NO:1, or in a nucleotide sequence at least 80% identical to SEQ ID NO:1.

8. The method according to claim 7, wherein the *Dirofilaria* spp. nematode is *Dirofilaria immitis*.

9. The method of claim 7 wherein the arsenic therapy is melarsomine dihydrochloride.

10. The method of claim 7 wherein the macrocyclic lactone is selected from the group consisting of ivermectin, selamectin, milbemycin oxime and moxidectin.

11. The method of claim 7 wherein the antibiotic is tetracycline.

12. The method of claim 11 wherein the tetracycline is doxycycline.

13. A method for treating an animal infected with a *Dirofilaria* spp. nematode, the method comprising: determining the genotype of said nematode at a position in a P-glycoprotein gene of said nematode corresponding to position 11 in SEQ ID NO:1 or a nucleotide sequence at least 80% identical to SEQ ID NO:1, or corresponding to positions 11 and 618 in SEQ ID NO:1 or a nucleotide sequence at least 80% identical to SEQ ID NO:1, wherein said determining comprises the use of a probe which binds to a nucleotide sequence corresponding to position 11 in SEQ ID NO:1, or a nucleotide sequence at least 80% identical to SEQ ID NO:1 or which binds to a nucleotide sequence corresponding to positions 11 and 618 of SEQ ID NO:1 or a nucleotide sequence at least 80% identical to SEQ ID NO:1; or which binds to a position in P-glycoprotein corresponding to position 11 of SEQ ID NO:1, or a sequence at least 80% identical to SEQ ID NO:1 or a position in P-glycoprotein corresponding to position 11 and 618 of SEQ ID NO:1, or a nucleotide sequence at least 80% identical to SEQ ID NO:1 and administering to said animal an adjusted dosage of a macrocyclic lactone, or administering an arsenic therapy, diethylcarbamazine, antibiotics, or a combination of one or more thereof, if the nematode of said infected animal has the genotype GG at a position in the P-glycoprotein gene corresponding to position 11 in SEQ ID NO: 1 or a nucleotide sequence at least 80% identical to SEQ ID NO:1; or corresponding to positions 11 and 618 in SEQ ID NO:1, or in a nucleotide sequence at least 80% identical to SEQ ID NO:1.

14. The method of claim 13 wherein said *Dirofilaria* spp. nematode is *Dirofilaria immitis*.

15. The method of claim 13 wherein the macrocyclic lactone is selected from the group consisting of ivermectin, selamectin, milbemycin oxime and moxidectin.

16. The method of claim 13 wherein the arsenic therapy is melarsomine dihydrochloride.

17. The method of claim 13 wherein the antibiotic is tetracycline.

18. The method of claim 17 wherein the tetracycline is doxycycline.

* * * * *

SEQUENCE LISTING

```
<160> NUMBER OF SEQ ID NOS: 6

<210> SEQ ID NO 1
<211> LENGTH: 623
<212> TYPE: DNA
<213> ORGANISM: Dirofilaria immitis

<400> SEQUENCE: 1
cgaaatccaa rgatattatt gcttgatgaa gcgaccagtg cattagatgc ggaaagtgaa      60
agagttagct tttttaattt taaattttta atctcttgga actattgaat gattttaat     120 tcactattct tttagtcacg aaaaattagt tggtttcaaa aaattctata attttaaaaa     180
gtctttcgca gagattattt catgtacaat ttaatatctt catgaaaaat taggattaat     240
atttgttagg ataatcagct aaactgaata taatctagca aattttttca atcattagaa     300
ataaggaaca tgaggtaaaa aaatatgtga atattgcgaa tacttttgaa ttgcctttt      360 tcttagtaat tctcattatc atagtttcat ttcagacagt tcaacaagct ttggacgttg     420
caagtagcgg tcgaacatgt attacagttg cacatagact atcatccatt cagtttgcag     480
atcagatatt ttttgtagaa aatggaaaag tagttgagca gggaacacat caagagctca     540
ttgaattgga cgggaagtac gctgatttaa ctcgcaaaca agatttgagg tcataaatgg     600
tcagaaatga agataatrtg gta                                             623

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggacaattat ccggtggtca                                                  20
```

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tcgcaaattt ccttccactt                                                    20

<210> SEQ ID NO 4
<211> LENGTH: 3445
<212> TYPE: DNA
<213> ORGANISM: Dirofilaria immitis

<400> SEQUENCE: 4
ggagagaatg agagaaatag ttcacgttca agctggtcag tgtggcaatc aaattggtgc        60
caaggtatcg atttatctat taattctttt tgtctcttga gcaaatgact catcttttcg       120
taatattccc gagcgataat caataaatga ttgatttgtt catacatgta tagactatca       180
atggatgctg tcactttgtt cttttagaa ttttcgaaaa aaaattcttg aaaaaatcaa        240
aaaaaaatag gatgttattc attaaaatat ttcatttaat taaaaatcaa tcccaagaat       300
cttattccaa ttttttttcaa tgcttttatt cgtttgctat atttcttcga ttgtatcttc     360 cttcttttcca ttatttattc gtgtccggat gtaattgtaa tatatatctc aaagtcattt     420
gtcatttagc actttaatga gattctcaat aagatccttc atatcgaact atggggttgc      480
cttcttttat gtgataaata attgcccctt agttgtctgg aattgaaaca agatgtttta     540
agtgcaaacg tacattattt aaaggctttt ttttaaagat tgctgtttga aaattttaag     600
cgcaattttg atttttcagt tctgggaagt aatatcggat gagcatggca ttcagcctga     660
tggtacgtat aaaggtgatt cagatttgca aattgaacga atcaatgtct actataacga     720
agcaaatggt tggtttattg gattttttc tctttttttt gtttcctctg cttgctcaaa      780
tcattttccg tcttcgcacg ctcacatcac attatacata attcgatatg tacatgccta     840
ttcctattac accatagtct catatacaac cagttatcgt ctggcaccga gcattagtat     900
cgccaatgag gttcatcaga atgtcctcaa aataatatgt tcgaaagtta atgaacatt      960 gtctgcgtct cttttcaagg tctatagtga tggataaaat ttaggacata taatgggata    1020
gatggcatga actagttaga ttagatgaat tagtcgcatg gtcttacttt ctaatctctt    1080
ctttgcataa tggaatttga tattgaacta acattctct ggctatggtc ttttctgaca     1140
gattagtact tgtatttatt gacaaatttt aataggtgtc aatttgttta gaatactaca    1200
gtgcatcttc gcgttcattt ttgtatcatt tctattcgca gtttaataaa taataatat    1260 ttttctctaa caacagtatt gtgatgagga attttttta tatgtttagg tggcaaatat     1320
gtaccacgag cgatccttgt cgatctggaa cctggtacta tggattctat tcgaggaggt    1380
ggatttggtc aactgttccg accggataat ttcgtatttg acagagtgg agctggcaac     1440 aactgggcta agggacatta cacagaaggt gccgaattag ttgataacgt tttggacgta    1500
atacgaaaag aagctgaagg atgcgactgt cttcaggtgc aatttgtgga ttgttacgat    1560
tccttagcta ttttgaatgt gaatgtggtt ttgaacagcc tcatttttt tgaaaaaaat    1620 attaatgaat ttttcaggg attccaactg actcattcac ttggaggtgg tacaggttct    1680
ggtatgggaa cattgctat ctcgaagatc cgtgaggaat atccagatcg gattatgagc    1740 tcttttcgg ttgtgccatc acctaaagta tgtatatttg tgtcttaact agtttgattt    1800
aattttcttg gttcatacct tttcgttatt tagaagccat catttttattt gcttcaaatt   1860
```

| | |
|---|---|
| catgaatgaa gtgaacacta tctgacgaga tgattttaat ctgtccctat ttccttttga | 1920 |
| aatgcaaggt tggtttttca ggtatcagat gttgtgttgg aaccttacaa tgcaacgtta | 1980 |
| tcagtgcatc aattagttga aaacactgat gaaactttct gcattgataa tgaagcttta | 2040 |
| tatgatatct gcttccgaac attgaaattg acgaatccaa cttacggcga tctcaatcac | 2100 |
| ttgggtccgt tgattgagtc cgtctcttca tttattcttc atatctttgc taaacttcaa | 2160 |
| attgcggttt cttcaatcat gttttattta gtatctgtaa caatgtctgg agtaacaaca | 2220 |
| tgtttacgtt tccctggaca attaaatgcc gatcttcgta agcttgctgt taatatggta | 2280 |
| ccattcccac gtttgcattt cttcatgcct ggatttgctc ctctctctgc acgtggtgct | 2340 |
| gctgcttatc gggcactcaa tgttgctgag ctcactcaac aggttttgtt tttctttatc | 2400 |
| attagaattg agaacatgag cgccacaatc cctatttttc tatttaatat atcgttataa | 2460 |
| cagtacttt agattttttc agaagcgtat ttttcagat gtttgatgcc aaaaatatga | 2520 |
| tggcagcatg tgatccacgt catggccgtt atctgaccgt agctgctatg ttccgaggca | 2580 |
| gaatgtcgat gcgagtgagt taattttggt attcttcttg ttaaaactga aatggaaat | 2640 |
| gtggaaaact tttatctatc tgatcctggt ttttctttgt cttaatttaa attatagaag | 2700 |
| tagaattttg tctacgtatt tcttcaactg caattttttt gcaattaaag ggttttttt | 2760 |
| ttctggtgca aggattcctt tgtttaaag ctcgatttat tagttgaaag tttctgctaa | 2820 |
| attaatttt aggaagtaga cgagcaaatg atgcaagtgc agaataagaa ttcatcgtat | 2880 |
| ttcgttgaat ggattccgaa taacgtaaaa acagctgttt gcgatattcc accacgtggc | 2940 |
| ttgaagatga gcgcaacatt catcggcaat acaacagcca tacaagaact tttaaacgc | 3000 |
| atttctgaac agtttactgg taaaggattt tattatctgc tcacttgatt ggccaaaatt | 3060 |
| taggttttg acgactttgg gagaaggcat agtggatgtg aacatccat gaacttccac | 3120 |
| tctaaaagag agcagtttga ttcgattttg ttttattca gctatgttcc gacgtaaagc | 3180 |
| attcttgcat tggtatactg gagaaggtat ggatgaaatg gaattcacgg aagcagagag | 3240 |
| taacatgaat gacttggtgt ctgaatatca gcaatatcag gatgcaacgt ctgatgaaga | 3300 |
| cggtgatctt caggaaggtg aatcggaata tattgagcaa gaggaataaa tacaacatga | 3360 |
| ttaattttat gaaaaaaaaa agaaaaaaca gaaatgtttc agtttttaa ttctcgtctt | 3420 |
| cttcatgttt tgtgttgtta caatt | 3445 |

<210> SEQ ID NO 5
<211> LENGTH: 751
<212> TYPE: DNA
<213> ORGANISM: Dirofilaria immitis

<400> SEQUENCE: 5

| | |
|---|---|
| ggacgggcgc gcttcaatgc tgtacggtgt ggatacttta gctgatgcag ttgcggtaac | 60 |
| tatgggacca aaggttatta atgtatttga tattttccg attcttaatc agcatactct | 120 |
| gaattgtgtt aaatgaatga taagcatgac tgaagaattg aaattttatt ctgaatatat | 180 |
| taggtcatct tggtaagcct tcgcaatctc acaatcaaaa cttttatgca ggatcataag | 240 |
| tcctatttgt gatagtgttc tagggaagaa atgtcgtaat cgaacagtca tggggaagtc | 300 |
| caaagatcac aaaggatggt gttactgtag cgaaagcgat cgatttcaaa gataaataca | 360 |
| agaatctggg agcaaaactg gtgcaggtaa gtagaaacaa atttatgaaa ttgcttttgg | 420 |
| actttcatgt aatacgattt aagtcggggc agttttagcg attgatagca agatagagac | 480 |
| tgatgataaa tgaatagtta tcgtcgaaga atttgtttcc tgatccagtt tttatcattt | 540 |

```
atctggagtg ggaatgagta gactttgaaa attgtttttg cttcactgtt tgattgtttc      600
aggatgtagc aaataaaacc aatgaagaag ctggagatgg tacgacatgc gctacagttt      660
tggcacgagc aattgcaaag gaaggtttcg aaaatatcag caaaggagct aatccagtgg      720
aagttcgacg aggtatattt agatttattt t                                    751

<210> SEQ ID NO 6
<211> LENGTH: 623
<212> TYPE: DNA
<213> ORGANISM: Dirofilaria immitis

<400> SEQUENCE: 6
cgaaatccaa agatattatt gcttgatgaa gcgaccagtg cattagatgc ggaaagtgaa       60
agagttagct tttttaattt taaattttta atctcttgga actattgaat gatttttaat      120
tcactattct tttagtcacg aaaaattagt tggtttcaaa aaattctata attttaaaaa      180
gtctttcgca gagattattt catgtacaat ttaatatctt catgaaaaat taggattaat      240
atttgttagg ataatcagct aaactgaata taatctagca aattttttca atcattagaa      300
ataaggaaca tgaggtaaaa aaatatgtga atattgcgaa tacttttgaa ttgccttttt      360
tcttagtaat tctcattatc atagtttcat ttcagacagt tcaacaagct ttggacgttg      420
caagtagcgg tcgaacatgt attacagttg cacatagact atcatccatt cagtttgcag      480
atcagatatt ttttgtagaa aatggaaaag tagttgagca gggaacacat caagagctca      540
ttgaattgga cgggaagtac gctgatttaa ctcgcaaaca agatttgagg tcataaatgg      600
tcagaaatga agataatgtg gta                                             623
```